US008400313B2

(12) United States Patent
Noguchi et al.

(10) Patent No.: US 8,400,313 B2
(45) Date of Patent: Mar. 19, 2013

(54) VEHICLE DRIVER SLEEP STATE CLASSIFICATION GENERATING DEVICE BASED ON HIDDEN MARKOV MODEL, SLEEP STATE CLASSIFICATION DEVICE AND WARNING DEVICE

(75) Inventors: Yoshihiro Noguchi, Hachioji (JP); Roongroj Nopsuwanchai, Kanagawa (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 831 days.

(21) Appl. No.: 12/522,505

(22) PCT Filed: Jan. 21, 2008

(86) PCT No.: PCT/JP2008/050730
§ 371 (c)(1),
(2), (4) Date: Jul. 8, 2009

(87) PCT Pub. No.: WO2008/088070
PCT Pub. Date: Jul. 24, 2008

(65) Prior Publication Data
US 2010/0036290 A1    Feb. 11, 2010

(30) Foreign Application Priority Data

Jan. 19, 2007   (JP) ................ 2009-009729

(51) Int. Cl.
*G08B 23/00* (2006.01)
*G08B 1/00* (2006.01)
*G08B 21/00* (2006.01)
*B60Q 1/00* (2006.01)
*G06F 19/00* (2006.01)

(52) U.S. Cl. ........ 340/576; 340/575; 340/532; 340/538; 340/540; 706/905; 701/116

(58) Field of Classification Search ................ 340/576
See application file for complete search history.

(56) References Cited

U.S. PATENT DOCUMENTS

| 4,611,199 A | * | 9/1986 | Seko et al. | ................ 340/576 |
| 4,725,824 A | | 2/1988 | Yoshioka | |

(Continued)

FOREIGN PATENT DOCUMENTS

| CN | 1662931 A | 8/2005 |
| CN | 101231690 A | 7/2008 |

(Continued)

OTHER PUBLICATIONS

European Search Report issued by EPO for corresponding European Patent Application No. 11168653.1 on Jul. 29, 2011.

(Continued)

*Primary Examiner* — Daniel Wu
*Assistant Examiner* — Muhammad Adnan
(74) *Attorney, Agent, or Firm* — Birch, Stewart, Kolasch & Birch, LLP

(57) ABSTRACT

There is provided an arousal state classification model generating device for generating a blink waveform pattern model and an arousal state pattern model based on data on a blink waveform, which are preferably used for accurately estimating an arousal level with respect to unspecified object persons, an arousal state classifying device for classifying the arousal state of an object person, and a warning device. In the arousal state classification model generating device, a first pattern model is generated by learning a statistical model by using as learning data first feature data extracted from the blink data of at least one of the eyes of each object person at the time of blinking and blink waveform identification information. A second pattern model is generated by learning a statistical model by using as learning data second feature data including data on the occurrence ratio of each specific type of blink waveform in the sequence of analysis intervals and arousal state information data in which arousal state information indicating the arousal state of each object person is provided to each sequence of analysis intervals.

21 Claims, 20 Drawing Sheets

U.S. PATENT DOCUMENTS

| | | | |
|---|---|---|---|
| 5,311,877 A * | 5/1994 | Kishi | 600/545 |
| 5,566,067 A * | 10/1996 | Hobson et al. | 702/75 |
| 6,496,724 B1 * | 12/2002 | Levendowski et al. | 600/544 |
| 6,625,485 B2 * | 9/2003 | Levendowski et al. | 600/544 |
| 6,927,694 B1 * | 8/2005 | Smith et al. | 340/576 |
| 7,233,933 B2 * | 6/2007 | Horvitz et al. | 706/21 |
| 7,403,124 B2 * | 7/2008 | Arakawa et al. | 340/576 |
| 7,415,139 B2 | 8/2008 | Takiguchi | |
| 7,519,512 B2 * | 4/2009 | Spence et al. | 702/189 |
| 7,592,820 B2 * | 9/2009 | Laakso et al. | 324/713 |
| 7,689,008 B2 * | 3/2010 | Hammoud et al. | 382/117 |
| 7,869,624 B2 | 1/2011 | Takiguchi | |
| 7,948,387 B2 * | 5/2011 | Ishida et al. | 340/575 |
| 8,036,736 B2 * | 10/2011 | Snyder et al. | 600/544 |
| 8,062,129 B2 * | 11/2011 | Pope et al. | 463/31 |
| 8,164,463 B2 * | 4/2012 | Omi | 340/575 |
| 2005/0180620 A1 | 8/2005 | Takiguchi | |
| 2007/0071209 A1 * | 3/2007 | Horvitz et al. | 379/201.06 |
| 2007/0116330 A1 | 5/2007 | Takiguchi | |
| 2007/0277198 A1 * | 11/2007 | Yasukawa et al. | 725/39 |
| 2008/0037837 A1 | 2/2008 | Noguchi et al. | |
| 2008/0118114 A1 | 5/2008 | Takiguchi | |
| 2011/0038511 A1 | 2/2011 | Takiguchi | |

FOREIGN PATENT DOCUMENTS

| | | |
|---|---|---|
| CN | 101520844 A | 9/2009 |
| EP | 1 503 330 A1 | 2/2005 |
| EP | 2 098 977 A1 | 9/2009 |
| JP | 60-592 A | 1/1985 |
| JP | 09-135826 | 5/1997 |
| JP | 10-272960 A | 10/1998 |
| JP | 11-056801 | 3/1999 |
| JP | 11-137530 | 5/1999 |
| JP | 2002-331850 A | 11/2002 |
| JP | 2003-331270 A | 11/2003 |
| JP | 2003-331271 A | 11/2003 |
| JP | 2007-312824 A | 12/2007 |
| KR | 2010-0022126 A | 2/2010 |
| WO | WO 03/096272 A1 | 11/2003 |
| WO | WO 2005/006034 A2 | 1/2005 |
| WO | WO-2005/114576 A1 | 12/2005 |

OTHER PUBLICATIONS

European Office Action, dated Feb. 11, 2011, for European Application No. 08703580.4.

Supplementary European Search Report, dated Feb. 2, 2011, for European Application No. 08703580.4.

Korean Office Action issued in application No. KR 10-2009-7014860 on Jan. 7, 2011.

* cited by examiner

F I G. 5
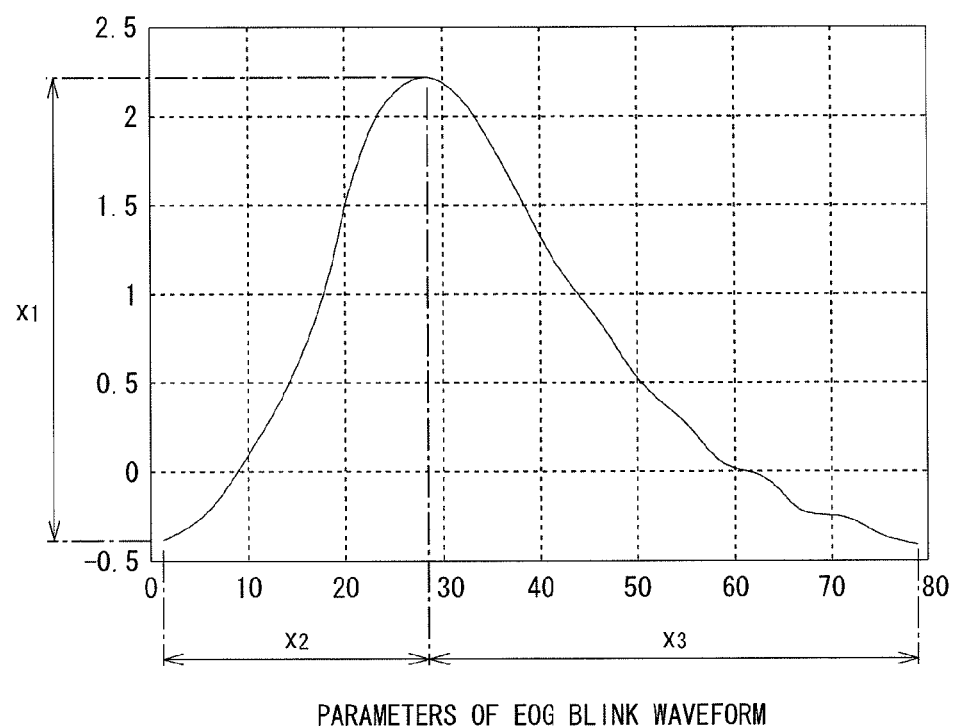
PARAMETERS OF EOG BLINK WAVEFORM

F I G. 7
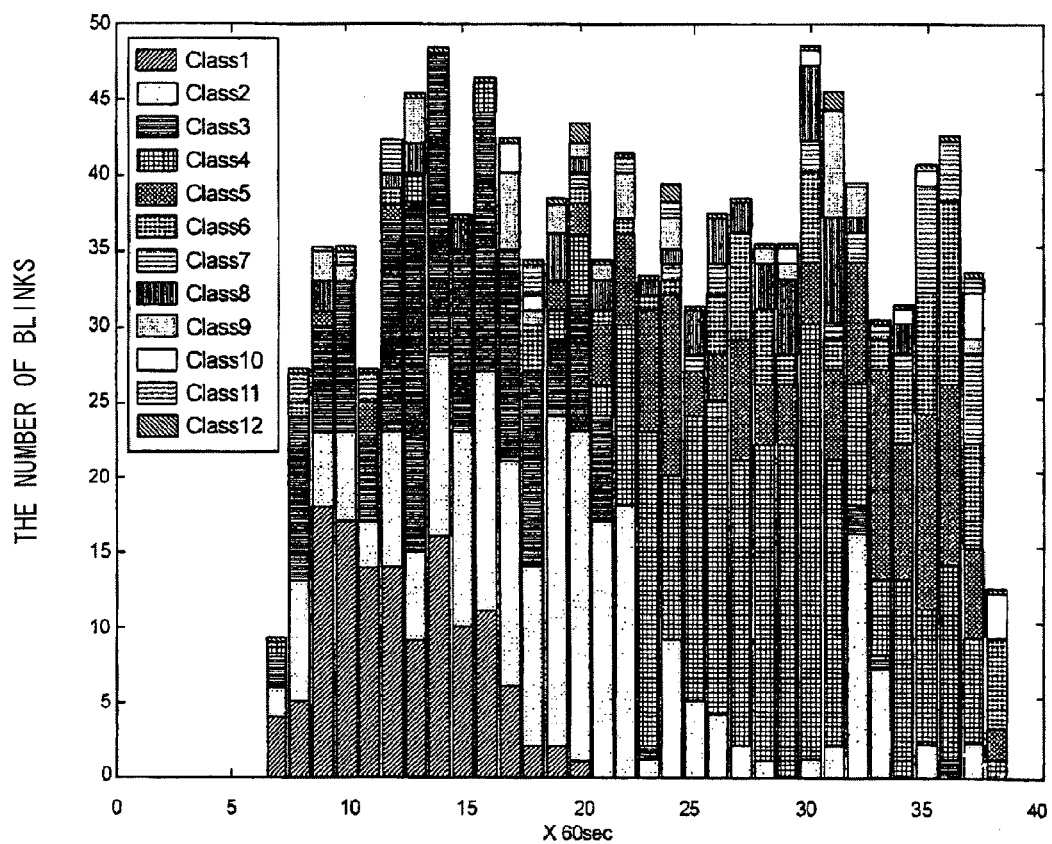

FIG. 8A

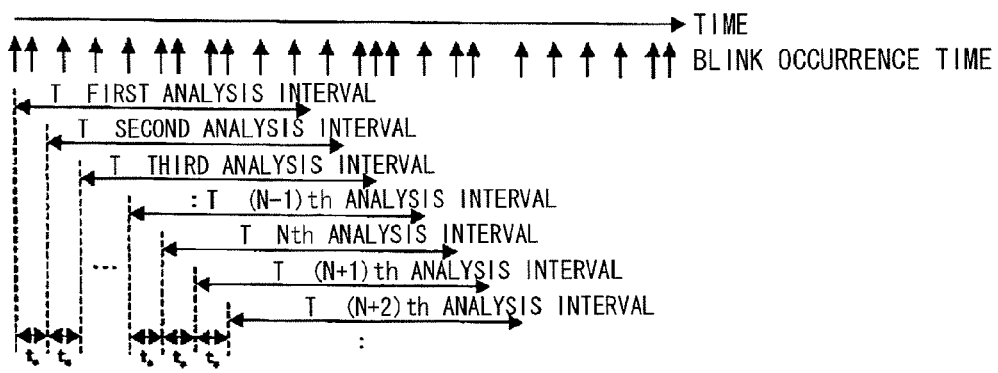

FIG. 8B

SECOND FEATURE COMPOSED OF N ANALYSIS INTERVALS
(FIRST TO Nth ANALYSIS INTERVALS)

SECOND FEATURE COMPOSED OF N ANALYSIS INTERVALS
(SECOND TO N+1th ANALYSIS INTERVALS)

BLINK TYPE

| | | | | | | | | | | | |
|---|---|---|---|---|---|---|---|---|---|---|---|
| 1 (Class1) | $R_{1,1}$ | $R_{2,1}$ | $R_{3,1}$ | | $R_{N-1,1}$ | $R_{N,1}$ | $R_{2,1}$ | $R_{3,1}$ | $R_{4,1}$ | | $R_{N,1}$ | $R_{N+1,1}$ |
| 2 (Class2) | $R_{1,2}$ | $R_{2,2}$ | $R_{3,2}$ | | $R_{N-1,2}$ | $R_{N,2}$ | $R_{2,2}$ | $R_{3,2}$ | $R_{4,2}$ | | $R_{N,2}$ | $R_{N+1,2}$ |
| 3 (Class3) | $R_{1,3}$ | $R_{2,3}$ | $R_{3,3}$ | | $R_{N-1,3}$ | $R_{N,3}$ | $R_{2,3}$ | $R_{3,3}$ | $R_{4,3}$ | | $R_{N,3}$ | $R_{N+1,3}$ |
| 4 (Class4) | $R_{1,4}$ | $R_{2,4}$ | $R_{3,4}$ | | $R_{N-1,4}$ | $R_{N,4}$ | $R_{2,4}$ | $R_{3,4}$ | $R_{4,4}$ | | $R_{N,4}$ | $R_{N+1,4}$ |
| 5 (Class5~7) | $R_{1,5}$ | $R_{2,5}$ | $R_{3,5}$ | | $R_{N-1,5}$ | $R_{N,5}$ | $R_{2,5}$ | $R_{3,5}$ | $R_{4,5}$ | | $R_{N,5}$ | $R_{N+1,5}$ |
| 6 (Class8) | $R_{1,6}$ | $R_{2,6}$ | $R_{3,6}$ | | $R_{N-1,6}$ | $R_{N,6}$ | $R_{2,6}$ | $R_{3,6}$ | $R_{4,6}$ | | $R_{N,6}$ | $R_{N+1,6}$ |
| 7 (Class9) | $R_{1,7}$ | $R_{2,7}$ | $R_{3,7}$ | | $R_{N-1,7}$ | $R_{N,7}$ | $R_{2,7}$ | $R_{3,7}$ | $R_{4,7}$ | | $R_{N,7}$ | $R_{N+1,7}$ |
| 8 (Class10~12) | $R_{1,8}$ | $R_{2,8}$ | $R_{3,8}$ | | $R_{N-1,8}$ | $R_{N,8}$ | $R_{2,8}$ | $R_{3,8}$ | $R_{4,8}$ | | $R_{N,8}$ | $R_{N+1,8}$ |

$R_{i,j}$: OCCURRENCE RATIO OF BLINK TYPE i IN jth ANALYSIS INTERVAL

FIG. 10A
FIG. 10B
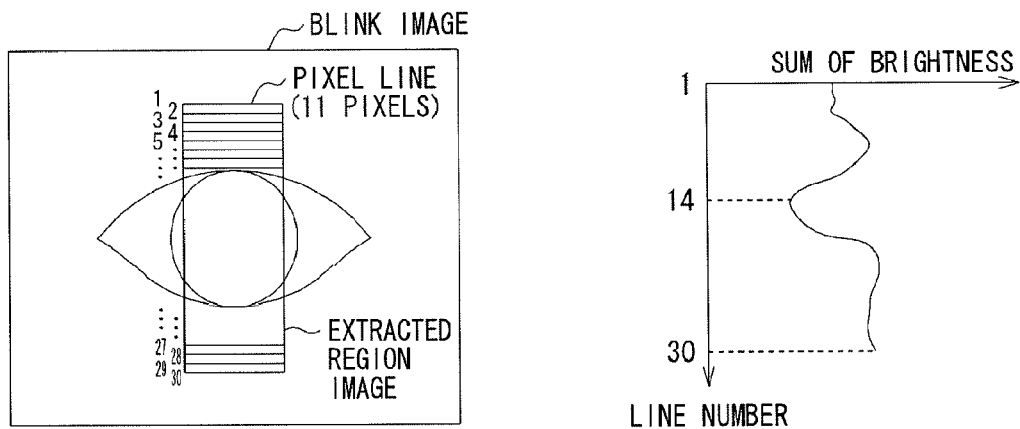
FIG. 11
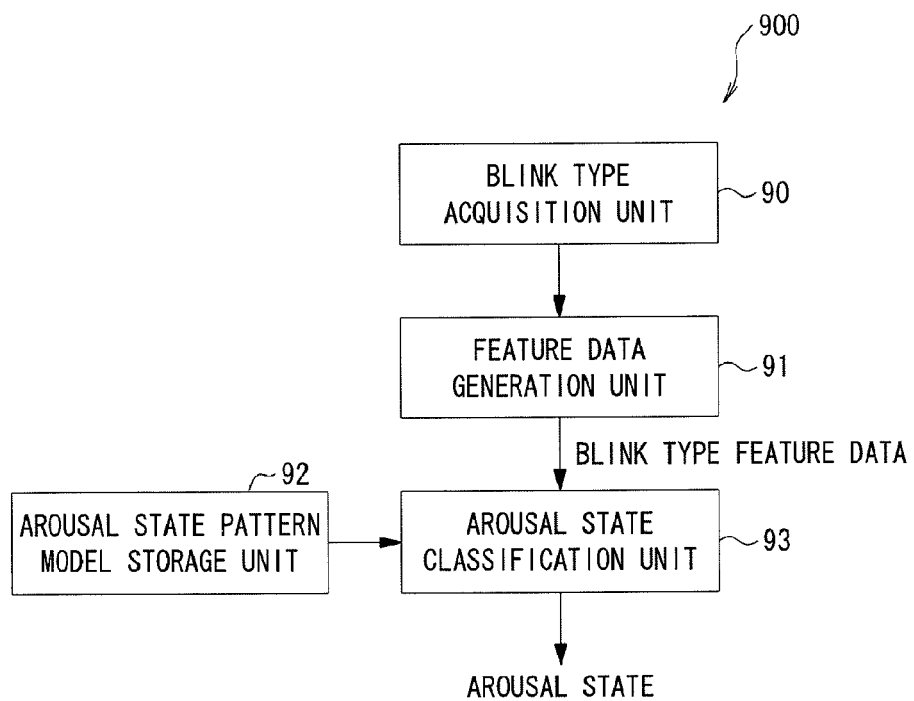

FIG. 18A

→ TIME

↑↑ ↑ ↑ ↑↑ ↑↑ ↑ ↑ ↑ ↑↑↑ ↑ ↑↑   ↑ ↑ ↑ ↑ ↑↑  BLINK OCCURRENCE TIME

T FIRST ANALYSIS INTERVAL
T SECOND ANALYSIS INTERVAL
T THIRD ANALYSIS INTERVAL
: T Mth ANALYSIS INTERVAL
T (N-1)th ANALYSIS INTERVAL
T Nth ANALYSIS INTERVAL

FIG. 18B

SECOND FEATURE COMPOSED OF N ANALYSIS INTERVALS
(FIRST TO Nth ANALYSIS INTERVALS) — 71
— 70

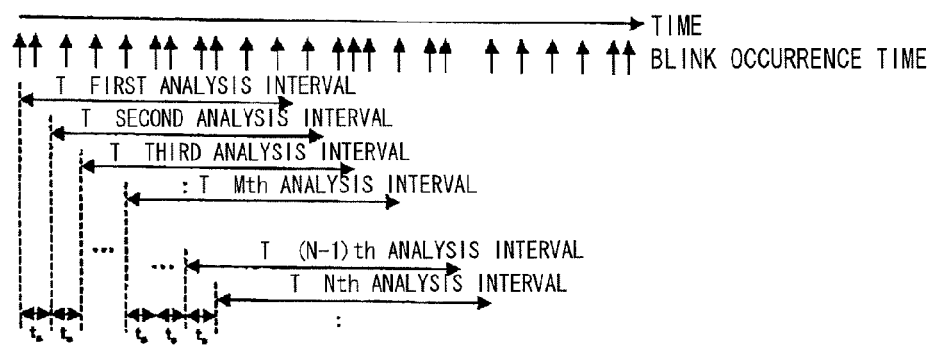

BLINK TYPE
1 (Class1)
2 (Class2)
3 (Class3)
4 (Class4)
5 (Class5~7)
6 (Class8)
7 (Class9)
8 (Class10~12)

$R_{i,j}$: OCCURRENCE RATIO OF BLINK TYPE $i$ IN $j$th ANALYSIS INTERVAL

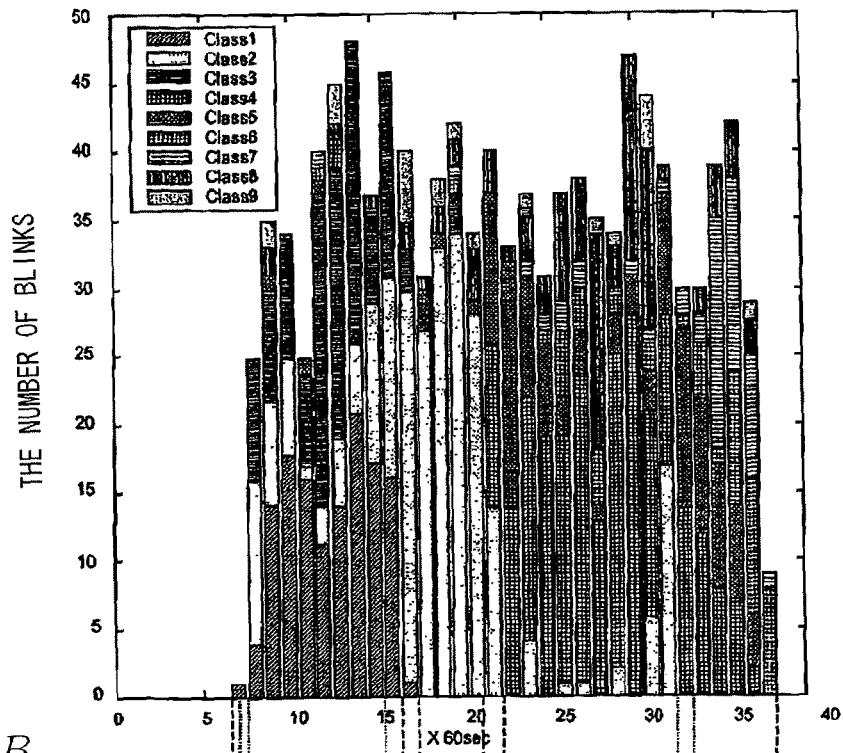

FIG. 22A
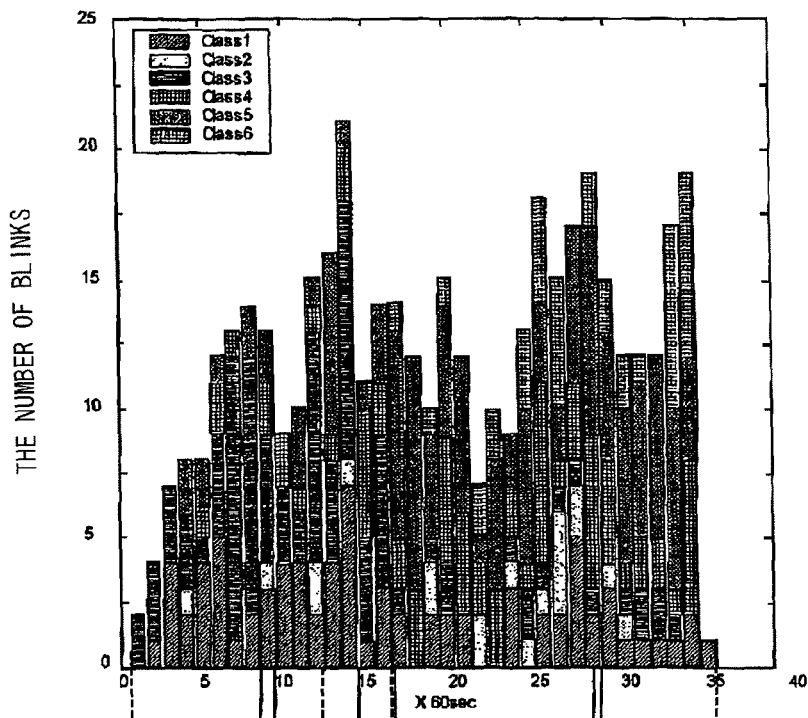
FIG. 22B
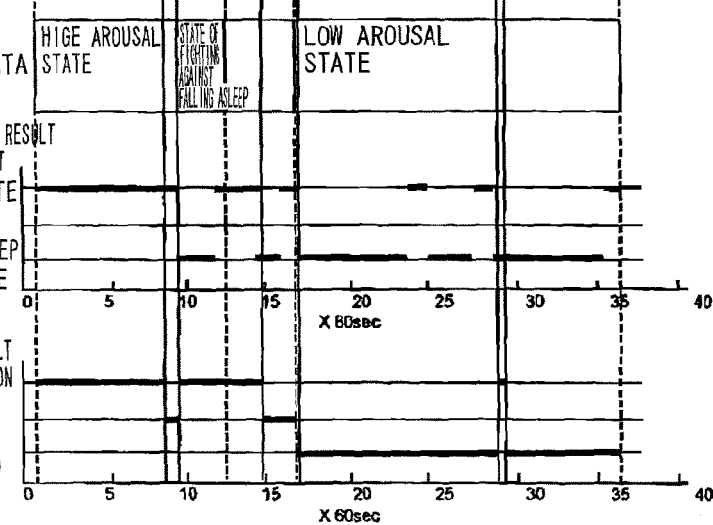
FIG. 22C
FIG. 22D

VEHICLE DRIVER SLEEP STATE CLASSIFICATION GENERATING DEVICE BASED ON HIDDEN MARKOV MODEL, SLEEP STATE CLASSIFICATION DEVICE AND WARNING DEVICE

TECHNICAL FIELD

The present invention relates to an arousal state classification model generating device for generating a blink waveform pattern model and an arousal state pattern model based on data on a physiological phenomenon, in particular, a blink waveform which is time variation of the degree of eye opening, an arousal state classifying device for classifying the arousal state of an object person based on data on the occurrence ratio of each of specific types of blink waveforms in the sequence of analysis intervals of the object person obtained by using the generated pattern models, and a warning device for warning the object person based on the classification result of the arousal state.

BACKGROUND ART

In recent years, the research and development of ITS (Intelligent Transport System) for practical use have been rapidly expanded along with the development and advancement of information processing technology, and more attention has been paid to the ITS as a new market by people in the industry.

Drive assist and navigation systems play a main role in the ITS. Here, it is desired that assistance and information presentation be made according to not only road and traffic situations and car behaviors but also characteristics and current state of a driver. Especially, estimation of the arousal level of a driver has long been studied. There have been conducted many researches using biological and physiological reaction such as brain waves, skin electrical activity, heart rate, and eye blink.

In particular, a blink occurrence pattern and the parameters of a waveform indicating an eye movement are known to vary according to the arousal level of an object person. Researches on detection of driver's drowsiness by use of the blink occurrence pattern and the parameters of the waveform indicating the eye movement at the time of blinking are now progressing.

Patent Document 1 discloses a behavior content classification device as a technique for classifying an arousal state by using the parameters of the waveform indicating the eye movement at the time of blinking.

The behavior content classification device includes an eye state classifying HMM (Hidden Markov Model) which outputs a likelihood for the type of blink waveform of an object person in relation to an input of features for video data of plural frames of an eye portion, and classifies the arousal state of the object person based on the likelihood output from the eye state classifying HMM in relation to the input of the features. A standard electro-oculogram (EOG) waveform in an arousal state and a typical electro-oculogram (EOG) waveform in a sleepy state are disclosed as the blink waveform associated with the arousal state.

In the related art disclosed in Patent Document 1, the type of the blink waveform is classified based on the parameters of the aperture, duration time and speed of a blink in each blink waveform at the time of generating the eye state classifying HMM.

Identification information for allowing identification of the type of the blink waveform is provided to the features extracted from the video data of plural frames of the eye portion corresponding to the blink waveform based on the classification result.

In addition, the HMM is learned by using the features to which the identification information is provided as described above as learning data.

Then, the HMM is generated for specific types of blinks, with which the arousal state can be sufficiently classified, out of various types of blink waveforms. The arousal state is classified based on a change in the occurrence frequencies of the specific types of blinks within a predetermined time.

To be more specific, the identification result of each blink waveform is histogram-processed in a predetermined time interval, thereby detecting the occurrence frequencies of blink patterns. When the occurrence frequency of a blink waveform that is not identified as the standard blink waveform in an arousal state becomes high, the arousal state is classified to become a low level.

Patent Document 1: International Publication No. WO2005/114576

DISCLOSURE OF THE INVENTION

Problems to be Solved by the Invention

In Patent Document 1, the inventors of the present invention have performed histogram processing on the identification result of each blink waveform in a predetermined time unit, and obtained the occurrence frequency change of each blink waveform pattern, thereby classifying the arousal state.

To be more specific, Patent Document 1 discloses that, for example, when the occurrence frequencies of plural specific types of blink waveform patterns become high, the arousal state of an object person is classified to become a low level.

However, the occurrence frequencies of the blink waveform patterns happening when the arousal state indicates a low level becoming high is employed as a single index based on the physiological knowledge. Thus, various arousal levels (states) occurring during transition from a high arousal state to a drowsy state are difficult to estimate.

Furthermore, each object person has a different estimation standard for the above index for estimating the arousal level (state), and even one object person has a different estimation standard for the above index depending on the object person's situation.

Accordingly, there has been a demand for accurate estimation of the arousal level which is applicable to unspecified object persons without being affected by the object person's situations.

The present invention has been made in view of such unsolved problems of the related art, and it is an object of the present invention to provide an arousal state classification model generating device for generating a blink waveform pattern model and an arousal state pattern model based on data on a blink waveform, an arousal state classifying device for classifying the arousal state of an object person based on data on the occurrence ratio of each of specific types of blink waveforms in the sequence of analysis intervals of the object person obtained by using the generated pattern models, and a warning device for warning the object person based on the classification result of the arousal state.

Although the blink and the arousal state are respectively cited as a physiological phenomenon and a physiological state, the present invention is not limited thereto.

Means for Solving the Problems

After filling the application of Patent Document 1, the present inventors found out that data including a time variation of the occurrence ratio or the number of occurrences of specific types of blink waveforms within a predetermined time interval has a characteristic pattern according to a change in arousal level by analyzing blink waveform data collected by changing the arousal level of an object person. The present inventors have thereby achieved the present invention which can solve the above problems based on the finding.

In order to achieve the above object, a physiological state classification model generating device according to an aspect of the present invention is a physiological state classification model generating device for generating a pattern model to determine a physiological state of an object person, characterized in that a physiological state pattern model modeled is generated by a statistical model based on physiological state information data obtained from physiological data and physiological phenomenon feature data including data on an occurrence ratio of each classification item of a physiological phenomenon so as to output a likelihood for physiological state information.

Moreover, in order to achieve the above object, the invention according to another aspect of the present invention, there is provided an arousal state classification model generating device for generating a pattern model to determine an arousal state of an object person, characterized in that an arousal state pattern model modeled by a statistical model is generated based on arousal state information data obtained from physiological data and blink type feature data including data on an occurrence ratio of each specific type of blink waveform so as to output a likelihood for arousal state information.

In order to achieve the above object, an arousal state classification model generating device according to yet another aspect of the present invention is an arousal state classification model generating device for generating a statistical model to determine an arousal state of an object person, the arousal state classification model generating device including: learning data storage means for storing first feature data extracted from blink data of at least one eye of each object person at the time of blinking, and blink waveform identification information data in which blink waveform identification information indicating a specific type of blink waveform is provided to each blink in the blink data; blink waveform pattern model generation means for learning a statistical model by using as learning data the first feature data and the blink waveform identification information data stored in the learning data storage means, and generating a first pattern model having as an input the first feature data and having as an output a likelihood for the blink waveform identification information in relation to the first feature data; feature data generation means for generating second feature data including data on an occurrence ratio of each of the specific types of blink waveforms in an analysis interval based on the blink waveform identification information data stored in the learning data storage means; and arousal state pattern model generation means for learning a statistical model by using as learning data the second feature data generated by the feature data generation means and arousal state information data in which arousal state information indicating the arousal state of the object person is provided to each sequence of the analysis intervals, and generating a second pattern model having as an input the second feature data and having as an output a likelihood for the arousal state information in relation to the second feature data.

Moreover, in order to achieve the above object, in the above configuration, the arousal state classification model generating device may be characterized in that the blink data is electro-oculogram (EOG) waveform data or moving picture of eye region.

Moreover, in order to achieve the above object, an arousal state classification model generating device in the above configuration may be characterized in that the data on the occurrence ratio is a change in the occurrence ratio or a change in the number of occurrences.

Moreover, in order to achieve the above object, the arousal state classification model generating device in the above configuration may be characterized in that an HMM (Hidden Markov Model) is used for the statistical model.

Moreover, in order to achieve the above object, the arousal state classification model generating device in the above configuration may be the arousal state classification model generating device further including: blink data storage means for storing the blink data of at least one eye of the object person at the time of blinking; feature data extraction means for extracting the first feature data from the blink data acquired from the blink data storage means; first pattern model storage means for storing the first pattern model generated by the blink waveform pattern model generation means; second feature data storage means for storing the second feature data generated by the feature data generation means; and second pattern model storage means for storing the second pattern model generated by the arousal state pattern model generation means.

Meanwhile, in order to achieve the above object, the arousal state classifying device in the above configuration may be an arousal state classifying device for classifying an arousal state of an object person, the arousal state classifying device including: blink data acquisition means for acquiring blink data of at least one eye of the object person at the time of blinking; a first pattern model generated by the arousal state classification model generating device;
first feature data extraction means for extracting first feature data corresponding to the first pattern model from the blink data acquired by the blink data acquisition means; blink waveform identification means for identifying a specific type of blink waveform corresponding to the first feature data extracted by the first feature data extraction means based on the first feature data and the first pattern model; second feature data generation means for generating second feature data including data on an occurrence ratio of each of the specific types of blink waveforms based on an identification result by the blink waveform identification means with respect to the blink data of the object person acquired in a sequence of analysis intervals; a second pattern model generated by the arousal state classification model generating device; and arousal state classification means for classifying the arousal state of the object person based on the second feature data generated by the second feature data generation means and the second pattern model.

Moreover, in order to achieve the above object, the arousal state classifying device in the above configuration may be characterized in that the blink data is data on an electro-oculogram (EOG) waveform or moving picture of eye region.

Moreover, in order to achieve the above object, in the above configuration may be characterized in that the data on the occurrence ratio is a change in the occurrence ratio or a change in the number of occurrences.

Moreover, in order to achieve the above object, the arousal state classifying device in the above configuration may be characterized in that an HMM (hidden Markov model) is used for the statistical model.

Moreover, in order to achieve the above object, a warning device may include: the arousal state classifying device; and warning means for warning the object person based on a classification result of the arousal state in the arousal state classifying device.

Moreover, in order to achieve the above object, a vehicle, includes the warning device.

Moreover, in order to achieve the above object, according to a further another aspect of the present invention, there is provided an arousal state classification model generating method for generating a statistical model to determine an arousal state of an object person, the arousal state classification model generating method including: a learning data storage step of storing first feature data extracted from blink data of at least one eye of each object person at the time of blinking, and blink waveform identification information data in which blink waveform identification information indicating a specific type of blink waveform is provided to each blink in the blink data; a blink waveform pattern model generation step of learning a statistical model by using as learning data the first feature data and the blink waveform identification information data stored in the learning data storage step, and generating a first pattern model having as an input the first feature data and having as an output a likelihood for the blink waveform identification information in relation to the first feature data; a feature data generation step of generating second feature data including data on an occurrence ratio of each of the specific types of blink waveforms in a sequence of analysis intervals based on the blink waveform identification information data stored in the learning data storage step; and an arousal state pattern model generation step of learning a statistical model by using as learning data the second feature data generated in the feature data generation step and arousal state information data in which arousal state information indicating the arousal state of the object person is provided to each of the sequences of analysis intervals, and generating a second pattern model having as an input the second feature data and having as an output a likelihood for the arousal state information in relation to the second feature data.

Moreover, in order to achieve the above object, the arousal state classification model generating method may be characterized in that the data on the occurrence ratio is a time variation of the occurrence ratio or a time variation of the number of occurrences.

Moreover, in order to achieve the above object, the arousal state classification model generating method in the above configuration may further include: a blink data storage step of storing the blink data of at least one eye of the object person at the time of blinking in blink data storage means; a feature data extraction step of extracting the first feature data from the blink data stored in the blink data storage means; a first pattern model storage step of storing the first pattern model generated in the blink waveform pattern model generation step;
a second feature data storage step of storing the second feature data generated in the feature data generation step; and a second pattern model storage step of storing the second pattern model generated in the arousal state pattern model generation step.

Moreover, in order to achieve the above object, according to a further another aspect of the present invention, there is provided an arousal state classifying method for classifying an arousal state of an object person, the arousal state classifying method including: a blink data acquisition step of acquiring blink data of at least one eye of the object person at the time of blinking; a first feature data extraction step of extracting first feature data corresponding to a first pattern model generated in the arousal state classification model generating method from the blink data acquired in the blink data acquisition step; a blink waveform identification step of identifying a specific type of blink waveform corresponding to the first feature data extracted in the first feature data extraction step based on the first feature data and the first pattern model; a second feature data generation step of generating second feature data including data on an occurrence ratio of each of the specific types of blink waveforms based on an identification result in the blink waveform identification step with respect to the blink data of the object person acquired in a sequence of analysis intervals; and an arousal state classification step of classifying the arousal state of the object person based on the second feature data generated in the second feature data generation step and a second pattern model generated in the arousal state classification model generating method.

Moreover, in order to achieve the above object, the arousal state classifying method in the above configuration may be characterized in that the data on the occurrence ratio is a time variation in the occurrence ratio or a time variation of the number of occurrences.

Moreover, in order to achieve the above object, according to a further another aspect of the present invention, there is provided an arousal state classification model generating program for generating a statistical model to determine an arousal state of an object person, causing a computer to function as: learning data storage means for storing first feature data extracted from blink data of at least one eye of each object person at the time of blinking, and blink waveform identification information data in which blink waveform identification information indicating a specific type of blink waveform is provided to each blink in the blink data; blink waveform pattern model generation means for learning a statistical model by using as learning data the first feature data and the blink waveform identification information data stored by the learning data storage means, and generating a first pattern model having as an input the first feature data and having as an output a likelihood for the blink waveform identification information in relation to the first feature data; feature data generation means for generating second feature data including data on an occurrence ratio of each of the specific types of blink waveforms in an analysis intervals based on the blink waveform identification information data stored by the learning data storage means; and arousal state pattern model generation means for learning a statistical model by using as learning data the second feature data generated by the feature data generation means and arousal state information data in which arousal state information indicating the arousal state of the object person is provided to each of the sequences of analysis intervals, and generating a second pattern model having as an input the second feature data and having as an output a likelihood for the arousal state information in relation to the second feature data.

Moreover, in order to achieve the above object, the arousal state classification model generating program in the above configuration may be characterized in that the data on the occurrence ratio is a time variation of the occurrence ratio or a time variation of the number of occurrences.

Moreover, in order to achieve the above object, the arousal state classification model generating program in the above configuration may further include: blink data storage means for storing the blink data of at least one eye of the object person at the time of blinking; feature data extraction means for extracting the first feature data from the blink data stored in the blink data storage means; first pattern model storage means for storing the first pattern model generated by the blink waveform pattern model generation means; second feature data storage means for storing the second feature data generated by the feature data generation means; and second pattern model storage means for storing the second pattern model generated by the arousal state pattern model generation means.

Moreover, in order to achieve the above object, according to a further another aspect of the present invention, there is provided an arousal state classifying program for classifying an arousal state of an object person, causing a computer to function as: blink data acquisition means for acquiring blink data of at least one eye of the object person at the time of blinking; first feature data extraction means for extracting first feature data corresponding to a first pattern model generated in the arousal state classification model generating program from the blink data acquired in the blink data acquisition means; blink waveform identification means for identifying a specific type of blink waveform corresponding to the first feature data extracted in the first feature data extraction means based on the first feature data and the first pattern model; second feature data generation means for generating second feature data including a time variation of an occurrence ratio of each of the specific types of blink waveforms based on an identification result in the blink waveform identification means with respect to the blink data of the object person acquired in a sequence of analysis intervals; and arousal state classification means for classifying the arousal state of the object person based on the second feature data generated in the second feature data generation means and a second pattern model generated in the arousal state classification model generating program.

Moreover, in order to achieve the above object, the arousal state classifying program in the above configuration may be characterized in that the data on the occurrence ratio is a time variation of the occurrence ratio or a time variation of the number of occurrences.

Advantages of the Invention

As described above, with the physiological state classification model generating device according to an aspect of the present invention, there can be generated the physiological state pattern model modeled by the statistical model based on the physiological state information data (an arousal state, a fatigue degree, a tension state, or the like) obtained from the physiological data and the physiological phenomenon feature data including the data on the occurrence ratio of each classification item of the physiological phenomenon (brain waves, skin electrical activity, heart rate, eye blink, or the like). The arousal state of the object person can be classified by using the physiological state pattern model.

Also, with the arousal state classification model generating device, there can be generated the arousal state pattern model modeled by the statistical model based on the arousal state information data obtained from the physiological data and the blink type feature data including the data on the occurrence ratio of each classification item of a blink waveform. The arousal state of the object person can be classified by using the arousal state pattern model.

Also, with the arousal state classification model generating device, the arousal state classifying device, the arousal state classification model generating method, the arousal state classifying method, the arousal state classification model generating program, and the arousal state classifying program, the arousal state can be classified with high accuracy based on the data on the occurrence ratio of each of the specific types of blinks in the sequence of analysis intervals in addition to a change in the occurrence frequencies of the specific types of blinks within a predetermined time such as the occurrence frequencies of specific types of blinks and the blink bursts of a specific type of blink, which is considered as effective in classifying the arousal state from the perspective of physiology.

The data on the occurrence ratio of each of the specific types of blinks of the object person in the sequence of analysis intervals is obtained from the second feature data. Thus, an experiment is carried out in advance to obtain the arousal state information data in which the data on the occurrence ratio of each of the specific types of blinks is correlated with various arousal levels (states) transiting from a high arousal state to a drowsy state. Accordingly, there can be obtained an effect that the second pattern model for classifying various arousal levels (states) of the object person can be generated from the second feature data.

That is, the arousal state can be classified with high accuracy based on the data on the occurrence ratio of each of the specific types of blinks in the sequence of analysis intervals in addition to a change in the occurrence frequencies of the specific types of blinks within a predetermined time such as the occurrence frequencies of specific types of blinks and the blink bursts of a specific type of blink, which is considered as effective in classifying the arousal state from the perspective of physiology.

Also, with the arousal state classification model generating device, and the arousal state classifying device, since the electro-oculogram (EOG), which can acquire time variation of degree of eye opening as the blink data with high accuracy, is used, the pattern model capable of identifying the type of blink waveform with high accuracy can be generated. Also, since the moving picture of eye region, from which the blink data can be acquired in a non-contact manner without installing electrodes on the object person, is used, it becomes more convenient for the object person.

Also, with the arousal state classification model generating device, the arousal state classifying device, the arousal state classification model generating method, the arousal state classifying method, the arousal state classification model generating program, and the arousal state classifying program, the time variation of the occurrence ratio or the time variation of the number of occurrences is used as the data on the occurrence ratio. Therefore, the arousal state can be classified with higher accuracy based on the local time variation of the occurrence ratio or the number of occurrences of each of the specific types of blinks in the sequence of analysis intervals.

Also, with the arousal state classification model generating device, and the arousal state classifying device, since the well-known HMM is used as the statistical model, there can be obtained an effect that the pattern model capable of identifying the type of blink waveform can be generated with respect to a behavior content with a temporal concept such as the blink.

Here, the "HMM" is a statistical model of a time-series signal, and a non-constant time-series signal can be modeled by transiting among a plurality of constant signal sources. For example, voice changes in time length depending on the speaking speed and indicates a characteristic shape (referred to as spectrum envelope) on the frequency depending on the speech content, but the shape fluctuates depending on the speaker, the environment, and the contents. The HMM is a statistical model that can absorb such fluctuation.

Also, with the warning device and the vehicle, the warning means can give the object person a warning based on the classification result of the arousal state in the arousal state classifying device.

Accordingly, for example, the second feature data including the time variation of the occurrence ratio or the number of occurrences of each of the specific types of blink waveforms of a driver in an automobile in each predetermined time unit is generated in real time, so that the arousal level (state) of the driver transiting to a drowsy state before completely falling asleep, or the arousal level (state) of fighting against falling asleep can be detected, for example.

Therefore, there can be obtained an effect that an accident can be prevented from occurring by warning an object person who is likely to fall asleep with a warning sound or flashing lights.

BRIEF DESCRIPTION OF THE DRAWINGS

FIG. 5 is an explanatory view of parameters extracted from electro-oculogram (EOG) waveform data;

FIG. 7 is an explanatory view illustrating a state in which the occurrence frequency of each type of blink in a certain time interval varies as time goes by;

FIG. 8 is an explanatory view of a second feature;

FIG. 10 is an explanatory view of feature data extracted from moving picture of eye region;

FIG. 11 is a block diagram illustrating a configuration of an arousal state classifying device 900 according to the present invention;

FIG. 18 is a view illustrating a storage area for second feature data in the warning device 200;

FIG. 21 is a view illustrating an example of the occurrence frequency of each type of blink within a certain time interval and results of classifying the arousal state of an object person A according to the related art and the present invention when the blink waveform pattern models of unspecified object persons are used, in a case of using moving picture of eye region as blink waveform data; and FIG. 22 is a view illustrating an example of the occurrence frequency of each type of blink in a certain time interval and results of classifying the arousal state of an object person B according to the related art and the present invention when the blink waveform pattern models of unspecified object persons are used, in a case of using moving picture of eye region as blink waveform data.

| | |
|---|---|
| 100 | Arousal state classification model generating device |
| 200 | Warning device |
| 10 | Blink data storage unit |
| 11 | First feature data extraction unit |
| 12 | First learning data storage unit |
| 13 | Blink waveform pattern model generation unit |
| 14 | First pattern model storage unit |
| 15 | Feature data generation unit |
| 16 | Second learning data storage unit |
| 17 | Arousal state pattern model generation unit |
| 18 | Arousal state pattern model storage unit |
| 20 | Blink data acquisition unit |
| 21 | Blink waveform pattern model storage unit |
| 22 | Feature data extraction unit |
| 23 | Blink type identification unit |
| 24 | Feature data generation unit |
| 25 | Arousal state pattern model storage unit |
| 26 | Arousal state classification unit |
| 27 | Warning unit |
| 800 | Arousal state classification model generating device |
| 80 | Arousal state data storage unit |
| 81 | Arousal state pattern model generation unit |
| 900 | Arousal state classifying device |
| 90 | Blink type acquisition unit |
| 91 | Feature data generation unit |
| 92 | Arousal state pattern model storage unit |
| 93 | Arousal state classification unit |

BEST MODE FOR CARRYING OUT THE INVENTION

First Embodiment

In the following, a first embodiment of the present invention will be described with reference to the drawings. FIG. 1 to FIG. 10 illustrate an embodiment of an arousal state classification model generating device, an arousal state classification model generating program, and an arousal state classification model generating method according to the present invention.

First, an outline of the arousal state classification model generating device according to the present invention will be described with reference to FIG. 1.

Figure 1:
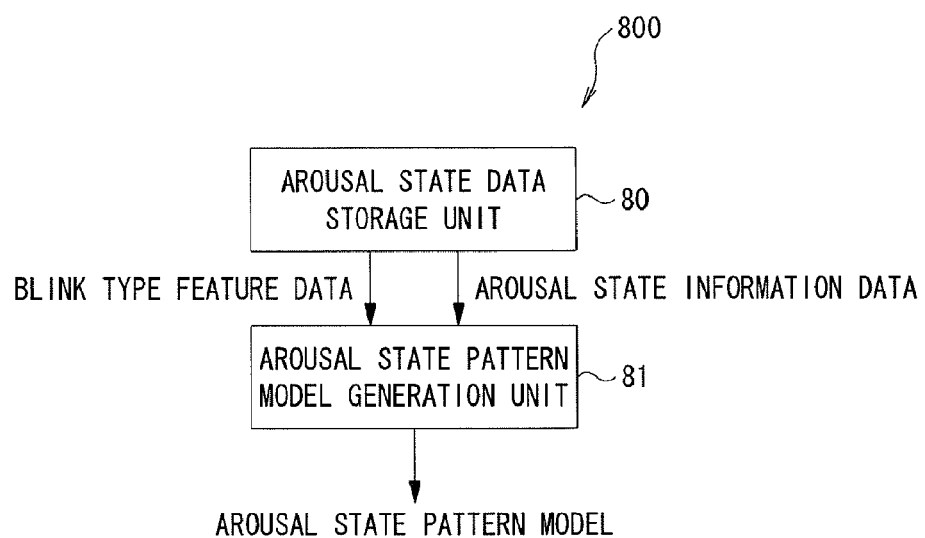
FIG. 1 is a block diagram schematically illustrating an arousal state classification model generating device 800 according to the present invention.

FIG. 1 is a block diagram schematically illustrating a configuration of an arousal state classification model generating device 800 according to the present invention.

An arousal state data storage unit 80 stores arousal state information data and blink type feature data, as learning data. To create the learning data, the electro-oculogram (EOG) waveform data of a plurality of types of blinks are collected by firstly measuring the eye blinks of a plurality of object persons, for example.

Blink waveform identification information for allowing identification of the classification item of a blink is also provided to each of the collected blinks, thereby creating physiological phenomenon classification item information data.

The occurrence ratio or the number of occurrences are obtained for each blink classification item in each analysis interval based on the physiological phenomenon classification item information data, and data composed of the occurrence ratio or the number of occurrences is created with respect to each analysis interval.

The sequence of the data corresponding to the sequence of successive analysis intervals is the blink type feature data.

Also, data, in which physiological state information indicating the arousal state of each object person is provided to each sequence of analysis intervals, is the arousal state information data. The arousal state of each object person is classified by using judgment based on physiological and biological data such as brain waves, skin surface potential, heart rate, and breathing rate, discrimination based on face expression, and an observation record and consideration, which are obtained at the time of collecting the electro-oculogram (EOG) waveform data.

An arousal state pattern model generation unit 81 stores the blink type feature data stored in the arousal state data storage unit 80 in a predetermined area of a storage device 40, which will be described later, as learning data.

The arousal state pattern model generation unit 81 further stores the arousal state information data in which the physiological state information indicating the arousal state of each object person is provided to each sequence of analysis intervals in a predetermined area of the storage device 40, as learning data.

The arousal state pattern model generation unit 81 learns a statistical model by using the blink type feature data and the arousal state information data stored in the storage device 40, as the learning data, and generates a pattern model for an arousal state (an arousal state pattern model).

A configuration of an arousal state classification model generating device according to the present invention will be described with reference to FIG. 2.

Figure 2:
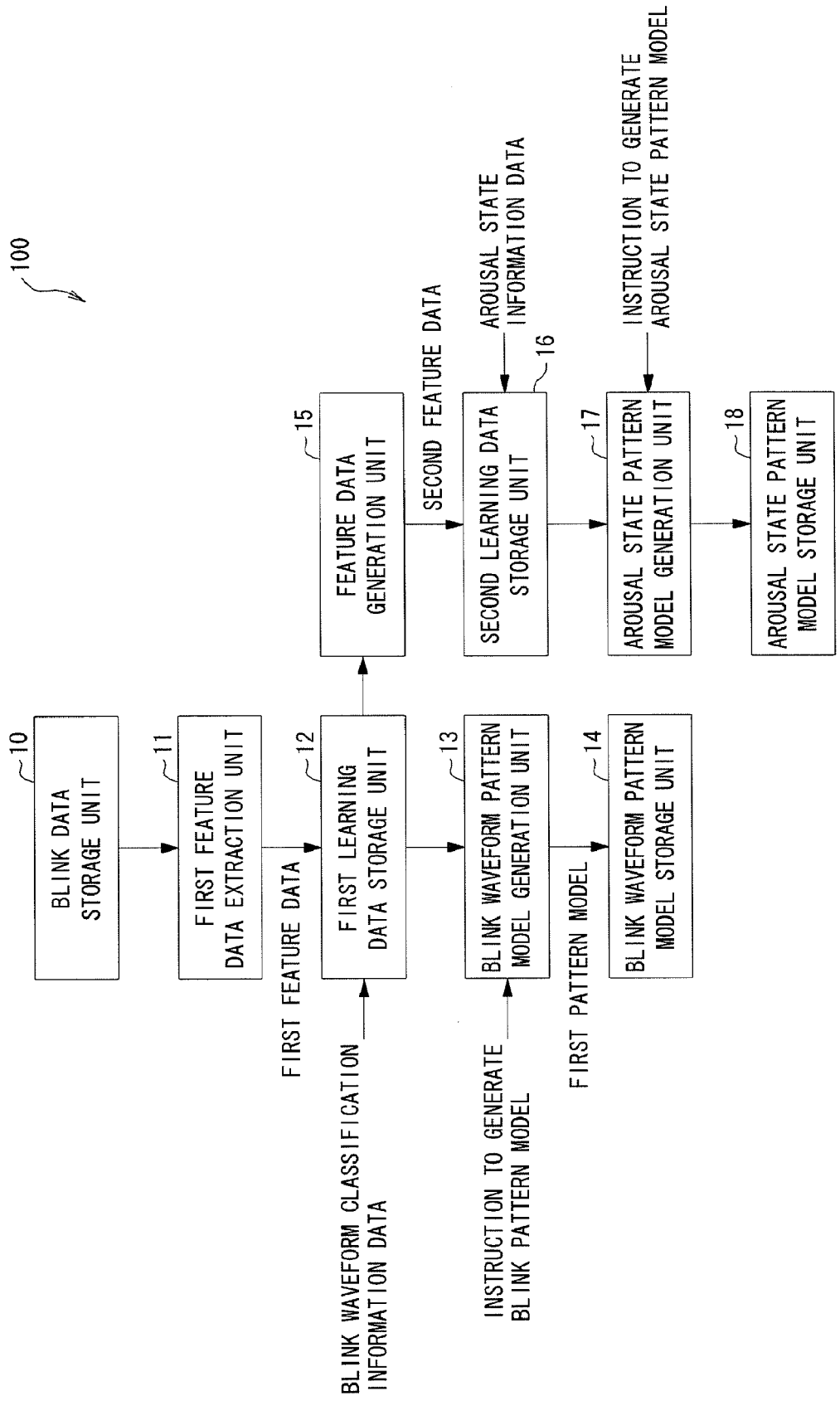
FIG. 2 is a block diagram illustrating a configuration of an arousal state classification model generating device 100 according to the present invention.

FIG. 2 is a block diagram illustrating a configuration of an arousal state classification model generating device 100 according to the present invention.

A blink data storage unit 10 stores the electro-oculogram (EOG) waveform data of a plurality of types of blinks obtained by measuring the eye blinks of a plurality of object persons in a predetermined area of a storage device 40, which will be described later, as learning data.

To be more specific, the blink data storage unit 10 stores the electro-oculogram (EOG) waveform data of the blinks of at least one of the left eye and right eye of an object person, for example. The blink data indicating a time variation of the degree of eye opening may also employ the moving picture of the blinks. The data of the moving picture includes at least one of the left eye and right eye of the object person at the time of blinking. The occurrence time of each blink waveform is also stored.

A first feature data extraction unit 11 extracts feature data as first feature data from the blink data stored by the blink data storage unit 10.

In the present embodiment, as will be described later, data obtained from three parameters of the distance data of the peak height of an electro-oculogram (EOG) waveform, the time data from start of blink to the peak height, and the time data from the peak height to end of blink is employed as the feature data.

Other feature data includes the maximum rise angle from the start of blink to the peak height, the maximum fall angle from the peak height to the end of blink, the duration time of a height of 50% or higher of the peak height, the duration time of a height of 75% or higher of the peak height, and a combination thereof.

In a case where the blink data is the moving picture of the blinks, the sum of brightness of each line in a predetermined region is calculated with respect to each frame of the moving picture data of the blinks, and the data on the sum of brightness of each blink video data is employed as the feature data.

The feature data further includes a frequency spectrum component obtained by converting the frequency of an eye region image, an inter-frame difference component between the current frame for the frequency spectrum component and its previous and subsequent frames, a Mel cepstrum (MFCC) component for an eye region image, an intra-frame moment component and an inter-frame moment component for an eye region image, and a combination thereof.

A first learning data storage unit 12 stores the first feature data extracted by the first feature data extraction unit 11 in a predetermined area of the storage device 40 described later as learning data.

The learning data storage unit 12 further stores blink waveform identification information data, in which blink waveform identification information for allowing identification of the type of blink is provided to each blink in the electro-oculogram (EOG) waveform data or the moving picture of the blinks stored in the blink data storage unit 10, in a predetermined area of the storage device 40 to be described later, as learning data.

A blink waveform pattern model generation unit 13 learns a statistical model by using the first feature data and the blink waveform identification information data stored by the first learning data storage unit 12 as the learning data, and generates a first pattern model that is a pattern model for a blink waveform (a blink waveform pattern model) according to an instruction to generate the blink waveform pattern model.

In the present embodiment, an HMM (hidden Markov model) is used as the statistical model.

A blink waveform pattern model storage unit 14 stores the first pattern model generated by the blink waveform pattern model generation unit 13 in a predetermined area of the storage device 40 to be described later.

A feature data generation unit 15 generates second feature data including a time variation of the occurrence ratio or the number of occurrences of each specific type of blink waveform in the sequence of analysis intervals based on the blink waveform identification information data stored by the first learning data storage unit 12.

A second learning data storage unit 16 stores the second feature data generated by the feature data generation unit 15 in a predetermined area of the storage device 40 described later as learning data.

The second learning data storage unit 16 further stores arousal state information data, in which arousal state information indicating the arousal state of each object person is provided to each sequence of analysis intervals, in a predetermined area of the storage device 40 to be described later, as learning data.

An arousal state pattern model generation unit 17 learns a statistical model by using the second feature data and the arousal state information data stored by the second learning data storage unit 16 as the learning data, and generates a second pattern model that is a pattern model for an arousal state (an arousal state pattern model) according to an instruction to generate the arousal state pattern model.

In the present embodiment, an HMM (hidden Markov model) is used as the statistical model.

An arousal state pattern model storage unit 18 stores the second pattern model generated by the arousal state pattern model generation unit 17 in a predetermined area of the storage device 40 described later.

Figure 3:
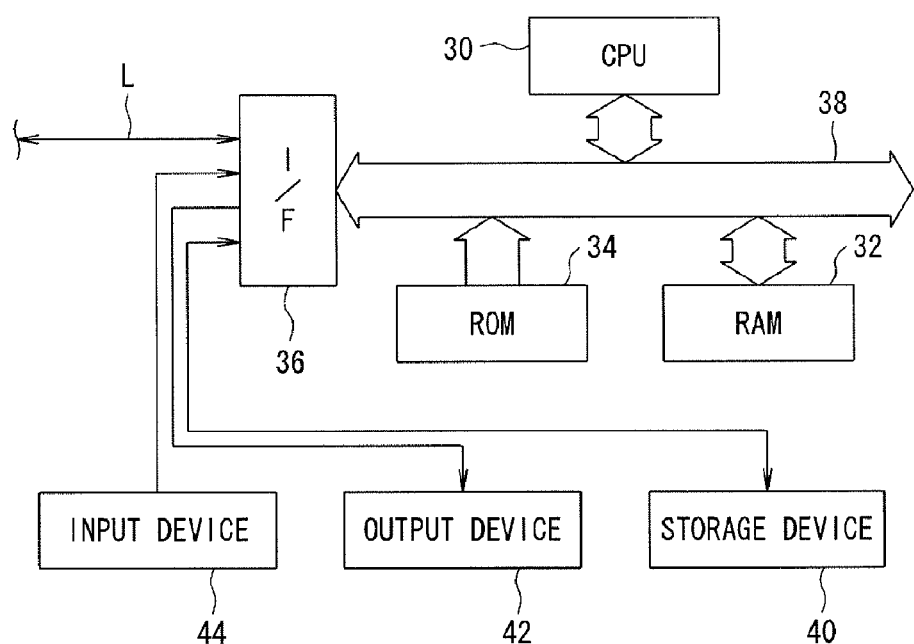
FIG. 3 is a block diagram illustrating a hardware configuration of the arousal state classification model generating device 100.

The arousal state classification model generating device 100 further includes a computer system for realizing the control of the aforementioned respective units on software. The hardware thereof is configured such that a CPU (central processing unit) 30 that is a processor for performing various controls and arithmetic processing, an RAM (random access memory) 32 that constitutes a main storage, and an ROM (read only memory) 34 that is a read-only storage are connected to one another via various internal and external buses 38 including a PCI (peripheral component interconnect) bus and an ISA (industrial standard architecture) bus, and an internal or external storage device (secondary storage) 40 such as an HDD (hard disk drive), an output device 42 such as printing means, CRT and LCD monitor, an input device 44 such as an operation panel, mouse, keyboard, and scanner, and a network to communicate with an external device, not shown, are connected to the buses 38 via an input and output interface (I/F) 36 as shown in FIG. 3.

When the arousal state classification model generating device 100 is powered ON, a system program such as a BIOS stored in the ROM 34 or the like loads various dedicated computer programs stored in advance in the ROM 34, or various dedicated computer programs installed on the storage device 40 via a storage medium such as a CD-ROM, DVD-ROM and flexible disk (FD) or via a communication network L such as the Internet, into the RAM 32. The CPU 30 performs predetermined control and arithmetic processing by using various resources according to a command described in the program loaded into the RAM 32. Accordingly, the functions of the respective means as described above can be realized on the software.

Operation of the First Embodiment

Next, a process flow for extracting the feature data from the blink waveform data in the arousal state classification model generating device 100 having the aforementioned configuration will be described with reference to FIG. 4.

Figure 4:
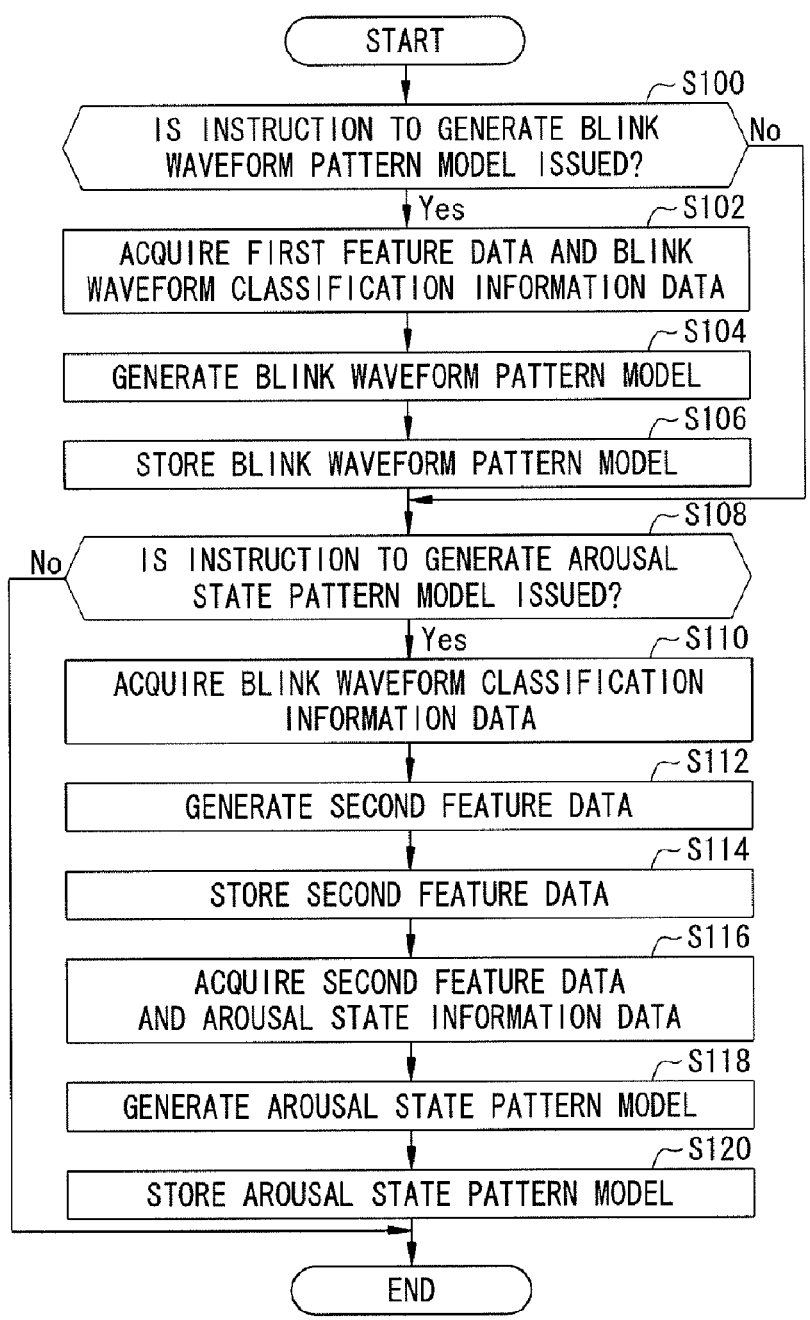
FIG. 4 is a flowchart illustrating a process of generating a first pattern model and a process of generating a second pattern model in the arousal state classification model generating device 100.

FIG. 4 is a flowchart illustrating a process of generating the first pattern model (the blink waveform pattern model) and a process of generating the second pattern model (the arousal state pattern model) in the arousal state classification model generating device 100.

As shown in the flowchart of FIG. 4, in the process of generating the first pattern model and the process of generating the second pattern model, the blink waveform pattern model generation unit 13 firstly classifies whether or not the instruction to generate the blink waveform pattern model is issued from a user via the input device 44 or the like in step S100. When it is classified that the generation instruction is issued (Yes), the process moves to step S102. When it is classified that the generation instruction is not issued (No), the process moves to step S108.

When the process moves to step S102, the blink waveform pattern model generation unit 13 acquires the first feature data and the blink waveform identification information data from the first learning data storage unit 12, and the process moves to step S104.

In step S104, the blink waveform pattern model generation unit 13 learns the statistical model by using the data acquired in step S102 as the learning data, and generates the first pattern model that is the blink waveform pattern model. The process then moves to step S106.

In step S106, the blink waveform pattern model generation unit 13 stores the first pattern model generated in step S104 in the predetermined area of the storage device 40 via the blink waveform pattern model storage unit 14, and the process moves to step S108.

In step S108, the arousal state pattern model generation unit 17 classifies whether or not the instruction to generate the arousal state pattern model is issued from the user via the input device 44 or the like. When it is classified that the generation instruction is issued (Yes), the process moves to step S110. When it is classified that the generation instruction is not issued (No), the process is terminated.

When the process moves to step S110, the blink waveform identification information data is acquired from the first learning data storage unit 12, and the process moves to step S112.

In step S112, the second feature data including the time variation of the occurrence ratio or the number of occurrences of each of the specific types of blink waveforms in the sequence of analysis intervals is generated based on the blink waveform identification information data acquired in step S110, and the process moves to step S114.

In step S114, the arousal state pattern model generation unit 17 stores the second feature data generated in step S112 in the predetermined area of the storage device 40 via the second learning data storage unit 16, and the process moves to step S116.

In step S116, the arousal state pattern model generation unit 17 acquires the second feature data and the arousal state information data from the second learning data storage unit 16, and the process moves to step S118.

In step S118, the arousal state pattern model generation unit 17 learns the statistical model by using the data acquired in step S116 as the learning data, and generates the second pattern model that is the arousal state pattern model. The process then moves to step S120.

In step S120, the arousal state pattern model generation unit 17 stores the second pattern model generated in step S118 in the predetermined area of the storage device 40 via the second pattern model storage unit 18, and the process is terminated.

Next, the operation of the present embodiment will be described in further detail with reference to FIG. 5 to FIG. 10.

To perform the process of extracting the first feature data and the process of generating the blink waveform pattern model described above in the arousal state classification model generating device 100, it is necessary to prepare the electro-oculogram (EOG) waveform data (the blink waveform data) of a plurality of types of blinks of a plurality of object persons in advance.

The blink waveform data is also used for performing the process of generating the second feature data and the process of generating the arousal state pattern model described above.

In the present embodiment, the electro-oculogram (EOG) waveforms of various blinks made in a high arousal state, a state of fighting against falling asleep, a low arousal state, and initiation of sleep by a plurality of object persons including healthy males and females of various ages, who gave informed consent, are measured in advance to collect the blink waveform data.

To obtain the electro-oculogram (EOG) waveforms (the EOG waveforms), electrodes are installed on the top and bottom lids of the right eye of an object person, and vertical EOG waveforms are measured at a sampling frequency of 250 Hz by using an AC amplifier for biopotential measurements (BIOPAC, time constant: 3.2 [sec], GAIN: 5000 times, a 3.5 [Hz] cut-off low-pass filter). Blink portions are detected from the vertical EOG waveforms.

The blink portions are detected by using a differential value (a first-order difference) of the EOG waveform in a similar manner to a well-known method (Hiroaki Yuze, Hidecki Tada: A computerized identification and date analysis of eye-blink EOG waves, Ergonomics, vol. 30, No. 5, p. 331-337, 1994), to set a point of time when the differential value exceeds a preset threshold for initiation as a blink start point, a point of time when the differential value exceeds a preset threshold for completion as a blink completion point, and a waveform between the start point and the end point as a blink waveform.

The blink waveform data collected as described above is stored in the blink data storage unit 10. The occurrence time of each of the detected blink waveforms is also stored in the blink data storage unit 10.

Next, the feature data extracted as the first feature data by the first feature data extraction unit 11 will be described. The parameters extracted from the acquired electro-oculogram (EOG) waveform data are converted to the feature data as will be described below.

FIG. 5 is an explanatory view of the parameters extracted from the blink waveform data in a case where the electro-oculogram (EOG) waveform data is used as the blink data.

The three parameters of the height (distance) data of the peak point of the waveform, the time data from the blink start point to the peak point, and the time data from the peak point to the blink end point are extracted from the blink waveform data.

For example, when the blink waveform data indicates a waveform with an eye-closing direction being oriented upward as shown in FIG. 5, a height x1 of the peak point is a differential value between the level (voltage or current) of the blink start point and the level of the peak point of the waveform. In the example of FIG. 5, the waveform peak is "x1 [mm]", a time period x2 (referred to as rise time x2 below) from the blink start point to the peak point is 28 [msec], and a time period x3 (fall time x3) from the peak point to the blink end point is 52 [msec].

In the present embodiment, a measured value is directly used as the height (distance) data x1 of the peak point, and logarithmically transformed values are used as the rise and fall time data x2 and x3. The three parameters x1, x2 and x3 are sequentially extracted from the acquired blink waveform data.

The feature parameters including the aforementioned three types of parameters x1 to x3 are normalized by using a Z-score method with respect to the measurement data of each of the object persons from who the blink waveform data is collected.

The normalization using the Z-score method is performed by normalizing the distributions of the three types of feature parameters x1 to x3 such that the respective average values are 0 and the respective standard deviations are 1.

To be more specific, an average value "$\mu$" of each of the feature parameters x1 to x3 is calculated. Also, a standard deviation "$\sigma$" of each of the feature parameters x1 to x3 is calculated.

Here, "X" represents each parameter in x1 to x3. The parameter "X" is converted to "z" according to the following expression (1).

[Expression 1]

$$z = \frac{X - \mu}{\sigma} \quad (1)$$

As a specific example using numerical values, when the average value of each of x1 to x3 of all the blink waveforms of an object person is (2.2239, 1.3542, 1.5693), and the standard deviation of each of x1 to x3 is (0.7396, 0.1000, 0.0709), "z" is calculated as shown in the following expression (2).

[Expression 2]

$$z = \left( \frac{2.9653 - 2.2239}{0.7396}, \frac{1.3222 - 1.3542}{0.1000}, \frac{1.5682 - 1.5693}{0.0709} \right) \quad (2)$$
$$= (1.0024, -0.3200, -0.0155)$$

"z" calculated with respect to each of the collected blink waveform data is employed as the first feature data. "z" is stored in the first learning data storage unit 12 as the learning data with respect to each blink in the electro-oculogram (EOG) waveform data stored in the blink data storage unit 10.

Next, the blink waveform identification information data stored in the first learning data storage unit 12, as the learning data, will be described.

The blink waveform identification information data is the data in which the blink waveform identification information for allowing identification of the type of blink is provided to each blink in the electro-oculogram (EOG) waveform data stored in the blink data storage unit 10.

Here, the blink waveform identification information is specifically a number for the identification of the type of blink classified as will be described below, for example. Not only the blink waveform identification information but also the occurrence time of each blink stored in the blink data storage unit 10 can be specified.

In the present embodiment, the type of blink is classified as follows according to the arousal level of an object person based on the physiological knowledge.

Figure 6:
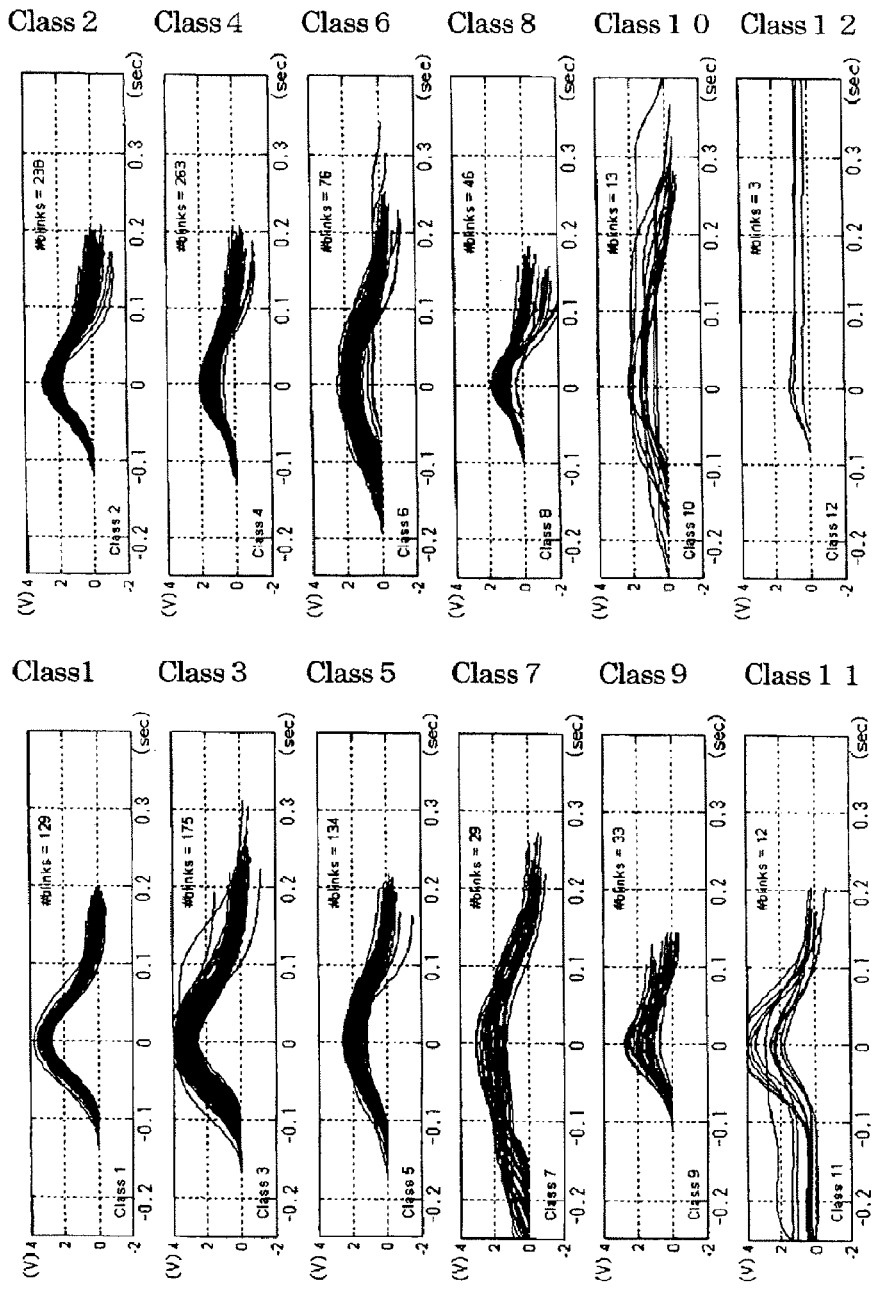
FIG. 6 is a view illustrating a classification result of electro-oculogram (EOG) waveforms by a clustering method using k-means.

FIG. 6 illustrates a result of classifying the electro-oculogram (EOG) waveform when the number of clusters is 12 by using k-means that is a well-known clustering method with respect to the first feature data "z" of an object person.

As shown in the present example, the number of clusters is larger than the blink classification number that is generally known. Accordingly, false detection and over-detection of an eye movement existing in the blink EOG waveform data can be classified into a cluster different from those of the blink, and thereby be excluded.

Class 1: Standard blink in a high arousal state
Class 2: Blink with a little smaller wave height with the eyelid falling due to sleepiness
Class 3: Strong and large blink intended to fight against falling asleep
Class 4: Blink with a very small wave height occurring in a low arousal state
Classes 5 to 7: Blink having a long duration time in a low arousal state
Class 8: Blink made during temporal arousal from a low arousal state
Class 9: Blink occurring in blink bursts
Classes 10 to 12: Falsely detected or excessively detected blink at the time of detecting the blink waveform (the one affected by an eye movement other than the blink, or the one difficult to determine whether it is the eye movement or blink.

In the above example, the 12 clusters are classified into 8 types of blinks. The blink waveform identification information indicates the type of blink into which each blink in the electro-oculogram (EOG) waveform data is classified.

When the instruction to generate the blink waveform pattern model is issued (the "Yes" branch from step S100), the blink waveform pattern model generation unit 13 acquires the first feature data and the blink waveform identification information data from the storage device 40 via the first learning data storage unit 12 (step S102).

The blink waveform pattern model generation unit 13 learns the statistical model by using the acquired first feature data and blink waveform identification information data as the learning data, and generates the blink waveform pattern model (the first pattern model) having as an input the first feature data and having as an output a likelihood for the types (8 types) of blinks in relation to the input first feature data (step S104).

In the present embodiment, the HMM is used as the statistical model.

The HMM is a probabilistic model of a time-series signal, and a non-constant time-series signal is modeled by transiting among a plurality of constant signal sources.

For example, a time period of one blink may change with the blink start point and end point fluctuating to some extent due to the detection state of the blink. Thus, the feature parameters in a time direction change accordingly.

Figure 17:
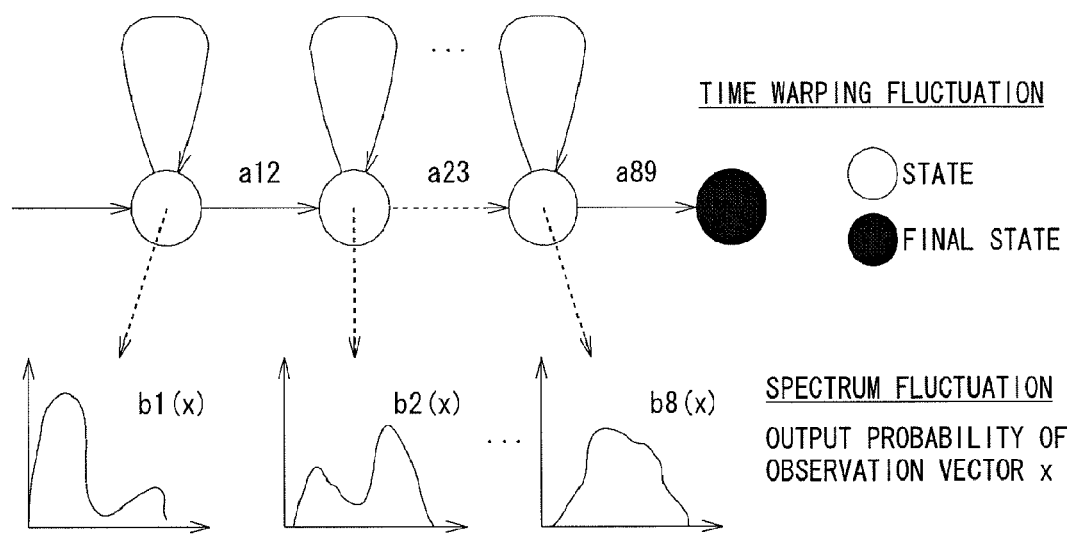
FIG. 17 is a view illustrating an example of an HMM.

Therefore, to be more specific, the HMM is learned by classifying the HMM having eight states, calculating the number of state transitions from the acquired feature parameters, and performing maximum likelihood estimation on a transition probability from a certain state to a subsequent state and an output probability of the feature parameters in the certain state based on the calculation result, as shown in FIG. 17.

The HMM having the transition probability and the output probability obtained by the learning is employed for the blink waveform pattern model (the first pattern model).

The blink waveform pattern model (the first pattern model) generated as described above is stored in the predetermined area of the storage device 40 via the blink waveform pattern model storage unit 14 (step S106).

When the instruction to generate the arousal state pattern model is issued (the "Yes" branch from step S108), the feature data generation unit 15 acquires the blink waveform identification information data from the storage device 40 via the first learning data storage unit 12 (step S110).

The occurrence time of each blink stored in the blink data storage unit 10 can be also specified.

Next, the feature data generated as the second feature data in the feature data generation unit 15 will be described.

FIG. 7 is an explanatory view illustrating a state in which the occurrence frequency of each type of blink within a certain time interval varies as time goes by with respect to the blink waveform data collected from a single object person.

When the time variation of the occurrence frequency of each type of blink is analyzed, the percentage of the blink in Class 1 that is the standard type of blink decreases, whereas the percentage of the blink in Class 2 that is the type of blink with a smaller peak height and the percentage of the blink in Class 3 that is the strong and large type of blink increase, from the start to the middle phase (about 20 minutes) of an experiment.

After 20 minutes, there are few blinks in Class 1 and Class 3, and the slow types of blinks in Classes 4 to 7 occupy the majority.

The quick and small types of blinks in Class 8 and Class 9 intermittently increase and decrease, but relatively increase in the latter half of the experiment.

According to the consideration and observation record of the experiment, the present object person felt slightly sleepy from the start of the experiment, and felt much sleepier from the middle phase to the latter half of the experiment.

Although the object person was temporarily awake due to an external factor, the arousal state is continuously lowered, and the object person fell asleep after the experiment.

From the correlation with the time variation of the features of the types of blinks and the correlation with moving picture recording, an eye-opening state in the blink in Class 2 is similar to an eye half-opening state in the standard blink in Class 1 in an arousal state, and is thus considered to be a state in which the eyelids are falling due to sleepiness.

Also, the strong and large blink in Class 3 that increases from the start to the middle phase of the experiment along with the increase in the blink in Class 2 is considered to be a blink intended to fight against falling asleep.

Since the arousal state of the object person is estimated to be significantly lowered from the middle phase to the final phase of the experiment, the blinks classified into Classes 4 to 7 are considered to be the waveforms in a low arousal state.

Accordingly, the state in which the occurrence ratio or the number of occurrences of each type of blink within a certain time interval varies as time goes by is taken as the target of pattern recognition, so that the arousal level of the object person can be classified.

In the present embodiment, the occurrence ratio of each type of blink is obtained in the sequence of analysis intervals, and the time variation of the occurrence ratio within a certain time interval is used as the feature data used for the pattern recognition.

FIG. 8A is an explanatory view illustrating the second feature data that is the aforementioned feature value.

A unit time (T in the drawing) and a predetermined number of blinks are defined as an analysis interval. The occurrence ratio of each type of blink is obtained at each certain time shift ($t_s$ in the drawing) while overlapping with the adjacent analysis interval.

A predetermined number (N in the drawing) of the occurrence ratios of each type of blink obtained as described above are merged, so as to generate the second feature data.

A predetermined number of the analysis intervals merged as described above is the sequence of analysis intervals. For example, the second feature data with respect to 8 types of blinks is shown in FIG. 8B.

Here, $R_{i,j}$ in FIG. 8B represents the occurrence ratio of a blink type i in the j-th analysis interval. In the present embodiment, the occurrence ratio of each type of blink is used. However, the number of occurrences of each type of blink may also be used to add the occurrence frequency of each blink to the feature (step S112).

Next, the arousal state information data stored by the second learning data storage unit 16, as the learning data, will be described. The arousal state information data is the data in which the arousal state information indicating the arousal state of an object person is provided to the second feature data stored in the second learning data storage unit 16.

Figure 9:
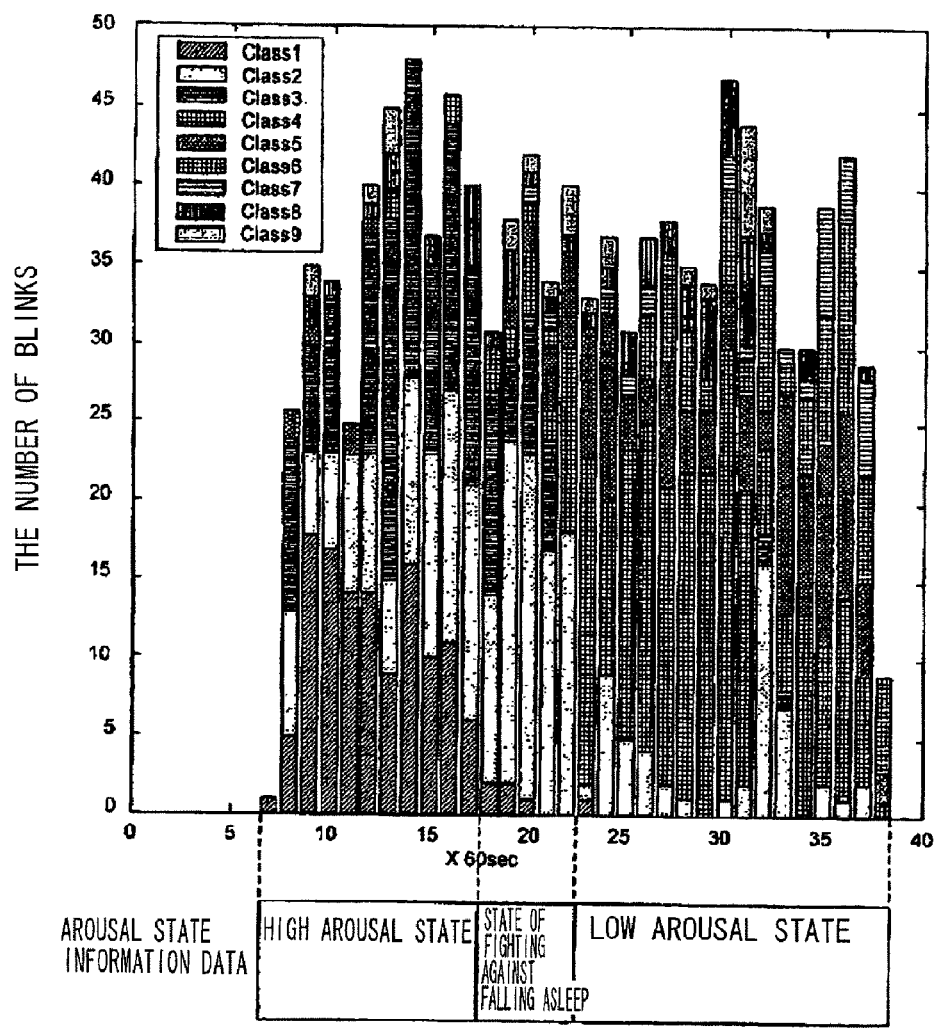
FIG. 9 is an explanatory view of arousal state information data.

In the present embodiment, the arousal state information data shown in FIG. 9 is used, in such a manner that the arousal state of an object person during an experiment is represented by three states of a high arousal state, a state of fighting against falling asleep, and a low arousal state based on a result speculated from the classification, consideration, and observation record using the physiological and biological data in the experiment. The blinks are classified into nine types.

In the present embodiment, the arousal state of the object person is represented by the three states of the high arousal state, the state of fighting against falling asleep, and the low arousal state, and the blinks are classified into nine types. However, the number of states and the classification number may be changed according to the application.

The arousal state pattern model generation unit 17 stores the generated second feature data in the predetermined area of the storage device 40 via the second learning data storage unit 16 (step S114).

Subsequently, the arousal state pattern model generation unit 17 acquires the second feature data and the arousal state information data from the storage device 40 via the second learning data storage unit 16 (step S116).

The arousal state pattern model generation unit 17 learns the statistical model by using the acquired second feature data and arousal state information data, as the learning data, and then generates the arousal state pattern model (the second pattern model) having as an input the second feature data and having as an output a likelihood for the arousal state information (step S118).

In the present embodiment, the HMM is used as the statistical model in a similar manner to the blink waveform pattern model (the first pattern model).

Although the electro-oculogram (EOG) waveform data is used as the blink waveform data, the case of using the moving picture of eye region instead of the electro-oculogram (EOG) waveform data will be described.

As a specific example, an extraction region image of 11 pixels in width and 30 pixels in height is trimmed from the moving picture of eye region with an eyeball portion as the center as shown in FIG. 10A. The sum of brightness values of each line (11 pixels in width) that constitutes the trimmed extraction region image is calculated. The data on the sum of brightness values of each of all the 30 lines of the extraction region image, which shows a feature as shown in FIG. 10B, for example, is generated.

In the present embodiment, the first feature data to be extracted from each blink waveform data is obtained by generating the data on the sum of brightness values with respect to the blink waveform data corresponding to one blink.

The first feature further includes a frequency spectrum component obtained by converting the frequency of an image of eye region, an inter-frame difference component between the current frame for the frequency spectrum component and its previous and subsequent frames, a Mel cepstrum (MFCC) component for an image of eye region, an intra-frame moment component and an inter-frame moment component for an image of eye region, and a combination thereof.

Also, the number of frames of the blink image data constituting each of the blink waveform data is changed according to the performance of shooting means and the type of blink (When a normal CCD camera (30 frames/second) is used, the number of frames is 8 to 11 with respect to one blink, for example.).

In the above-described first embodiment, the blink data storage unit 10 corresponds to blink data storage means. The first feature data extraction unit 11 corresponds to feature data means. The first learning data storage unit 12 corresponds to learning data storage means. The blink waveform pattern model generation unit 13 corresponds to blink waveform pattern model generation means. The blink waveform pattern model storage unit 14 corresponds to first pattern model storage means. The feature data generation unit 15 corresponds to feature data generation means. The second learning data storage unit 16 corresponds to second feature data storage means. The arousal state pattern model generation unit 17 corresponds to arousal state pattern model generation means. The arousal state pattern model storage unit 18 corresponds to second pattern model storage means. The arousal state pattern model generation unit 81 corresponds to an arousal state classification model generating device.

In the above-described first embodiment, steps S100 to S104 correspond to a step of generating a blink waveform pattern model. Step S106 corresponds to a step of storing a first pattern model. Steps S108 to S112 correspond to a step of generating feature data. Step S114 corresponds to a step of storing second feature data. Steps S116 to S118 correspond to a step of generating an arousal state pattern model. Step S120 corresponds to a step of storing a second pattern model.

Second Embodiment

Next, a second embodiment of the present invention will be described with reference to the drawings. FIG. 11 to FIG. 21 illustrate an embodiment of an arousal state classifying device, an arousal state classifying program, and an arousal state classifying method according to the present invention.

First, a configuration of the arousal state classifying device according to the present invention will be described with reference to the drawing. FIG. 11 is a block diagram illustrating a configuration of an arousal state classifying device 900 according to the present invention.

A blink type acquisition unit 90 acquires occurrence time information indicating the time when each blink waveform classified into each specific type of blink waveform occurs in each analysis interval in which the arousal state of an object person is changed.

A feature data generation unit 91 obtains the occurrence ratio or the number of occurrences of each blink classification item in each analysis interval based on the occurrence time information of each blink waveform acquired by the blink type acquisition unit 90, and creates data composed of the occurrence ratio or the number of occurrences with respect to each analysis interval. The data is blink type feature data.

An arousal state pattern model storage unit 92 stores the arousal state pattern model generated by the arousal state classification model generating device 800 in the above-described first embodiment.

An arousal state classification unit 93 classifies the arousal state of an object person based on the blink type feature data generated by the feature data generation unit 91 and the arousal state pattern model stored in the arousal state pattern model storage unit 92.

The arousal state to be classified includes a gradually changing state between a high arousal state in which the object person is completely awake and a drowsy state through a state of fighting against falling asleep and a low arousal state.

For example, the gradually changing state includes a normal high arousal state, a state of feeling sleepy, a state of fighting against falling asleep, a low arousal state in which the object person feels very sleepy, and a drowsy state.

Next, a warning device according to the present embodiment includes the blink waveform pattern model and the arousal state pattern model generated by the arousal state classification model generating device 100 in the above-described first embodiment, and identifies the arousal state of a driver in each sequence of analysis intervals by using the pattern models.

First, a configuration of the warning device according to the present invention will be described with reference to the drawing.

Figure 12:
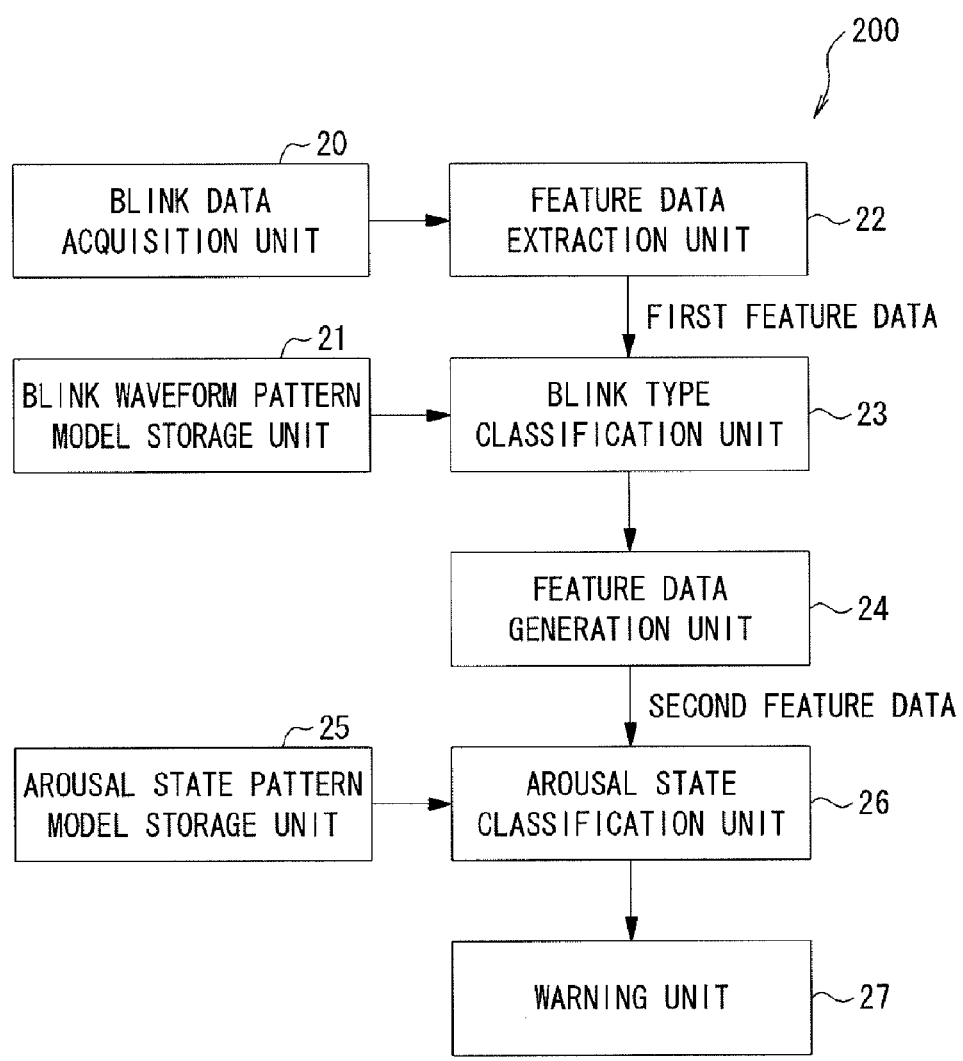
FIG. 12 is a block diagram illustrating a configuration of a warning device 200 according to the present invention.

FIG. 12 is a block diagram illustrating a configuration of a warning device 200 according to the present invention.

As shown in FIG. 12, the warning device 200 includes a blink data acquisition unit 20 for acquiring blink data including a time variation of the degree of eye opening of at least one eye of a driver, a blink waveform pattern model storage unit 21 for storing the blink waveform pattern model generated by the arousal state classification model generating device 100 in the above-described first embodiment, a feature data extraction unit 22 for extracting first feature data from the blink data acquired by the blink data acquisition unit 20, a blink type identification unit 23 for identifying the type of blink waveform based on the blink waveform pattern model stored in the blink waveform pattern model storage unit 21 and the first feature data extracted by the feature data extraction unit 22, a feature data generation unit 24 for generating second feature data based on the identification result of the type of blink waveform identified by the blink type identification unit 23, an arousal state pattern model storage unit 25 for storing the arousal state pattern model generated by the arousal state classification model generating device 100 in the above-described first embodiment, and an arousal state classification unit 26 for classifying the arousal state of an object person based on the second feature data generated by the feature data generation unit 24 and the arousal state pattern model stored in the arousal state pattern model storage unit 25.

The blink data acquisition unit 20 includes an AC amplifier for biopotential measurements, to measure vertical EOG (electro-oculogram (EOG) waveforms) in real time via electrodes installed on the top and bottom lids of a driver.

The blink waveform pattern model storage unit 21 stores the blink waveform pattern model generated by the arousal state classification model generating device 100 in the above-described first embodiment in a predetermined area of a storage device 60 described later.

The feature data extraction unit 22 extracts the first feature data obtained from three feature parameters of a peak height (distance) x1 of a blink waveform, a rise time x2 from blink start to the peak height, and a fall time x3 from the peak height to blink end, as the feature data from the blink electro-oculogram (EOG) waveform data (the blink waveform data) acquired by the blink data acquisition unit 20 in a similar manner to the above-described first embodiment.

The blink type identification unit 23 identifies the type of blink waveform based on the blink waveform pattern model stored by the blink waveform pattern model storage unit 21 and the first feature data extracted by the feature data extraction unit 22.

The feature data generation unit 24 generates the second feature data based on the identification result of the type of blink waveform identified by the blink type identification unit 23, and then outputs the second feature data to the arousal state classification unit 26.

That is, the occurrence ratio or the number of occurrences of the identification result of each type of blink is obtained in the sequence of analysis intervals first, and a time variation of the occurrence ratio or the number of occurrences in a certain time interval is used as the second feature data.

The arousal state pattern model storage unit 25 stores the arousal state pattern model generated by the arousal state classification model generating device 100 in the above-described first embodiment in a predetermined area of the storage device 60, as will be described later.

The arousal state classification unit 26 classifies the arousal state of an object person based on the second feature data generated by the feature data generation unit 24 and the arousal state pattern model stored by the arousal state pattern model storage unit 25.

The arousal state to be classified includes a gradually changing state between a high arousal state in which the object person is completely awake and a drowsy state through a state of fighting against falling asleep and a low arousal state.

For example, the gradually changing state includes a normal high arousal state, a state of feeling sleepy, a state of fighting against falling asleep, a low arousal state in which the object person feels very sleepy, and a drowsy state.

The warning device 200 further includes a warning unit 27 for warning a driver based on the classification result of the arousal state classification unit 26.

The warning unit 27 gives a driver a warning according to the content of the arousal state based on the classification result of the arousal state classification unit 26.

To be more specific, for example, the warning unit 27 outputs a voice message to recommend the driver to take a rest when the driver is classified to feel slightly sleepy. The warning unit 27 outputs a warning sound with a relatively loud sound volume when the driver is classified to be in the state of fighting against falling asleep. The warning unit 27 outputs a warning sound with a very loud sound volume or a strong message content when the driver is classified to be in the low arousal state in which the driver feels very sleepy or in the drowsy state.

Figure 13:
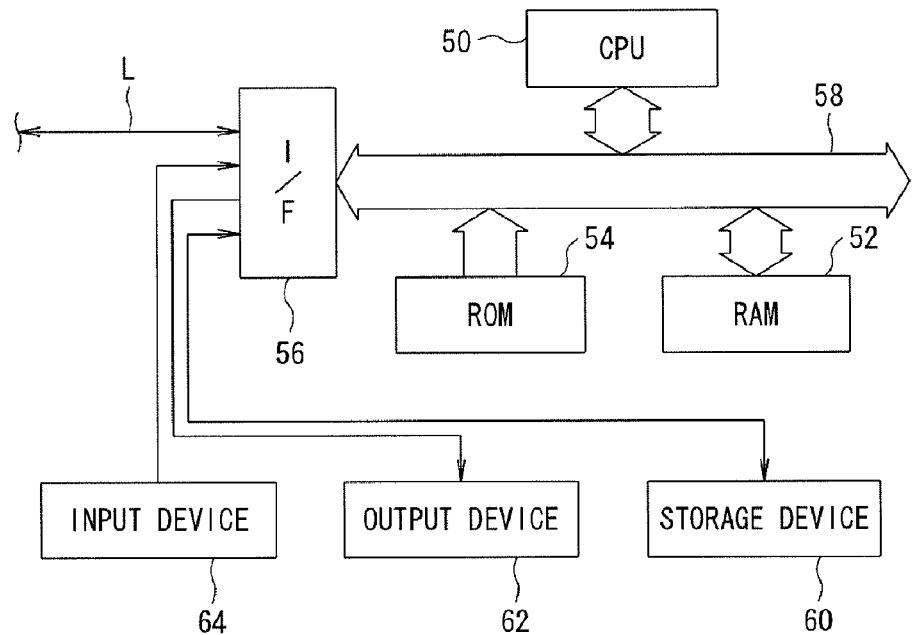
FIG. 13 is a block diagram illustrating a hardware configuration of the warning device 200.

The warning device 200 further includes a computer system for realizing the control of the above-described respective units on software. The hardware thereof is configured such that a CPU (central processing unit) 50 that is a processor for performing various control and arithmetic processing, an RAM (random access memory) 52 that constitutes a main storage, and an ROM (read only memory) 54 that is a read-only storage are connected to each other via various internal and external buses 58 including a PCI (peripheral component interconnect) bus and an ISA (industrial standard architecture) bus, and an internal or external storage device (secondary storage) 60 such as an HDD (hard disk drive), an output device 62 such as an LCD monitor, an input device 64 such as an operation panel and remote controller, and a network L to communicate with an external device, not shown, are connected to the buses 58 via an input and output interface (I/F) 56 as shown in FIG. 13.

When the warning device 200 is powered ON, a system program such as a BIOS stored in the ROM 54 or the like loads various dedicated computer programs stored in advance in the ROM 54, or various dedicated computer programs installed on the storage device 60 via a storage medium such as a CD-ROM, DVD-ROM and flexible disk (FD) or via the communication network L such as the Internet, into the RAM 52. The CPU 50 performs predetermined control and arithmetic processing by using various resources according to a command described in the program loaded into the RAM 52. Accordingly, the functions of the respective means as described above are realized on the software.

Operation of the Second Embodiment

Next, a process flow for extracting the first feature data in the warning device 200 having the above-described configuration will be described with reference to FIG. 14.

Figure 14:
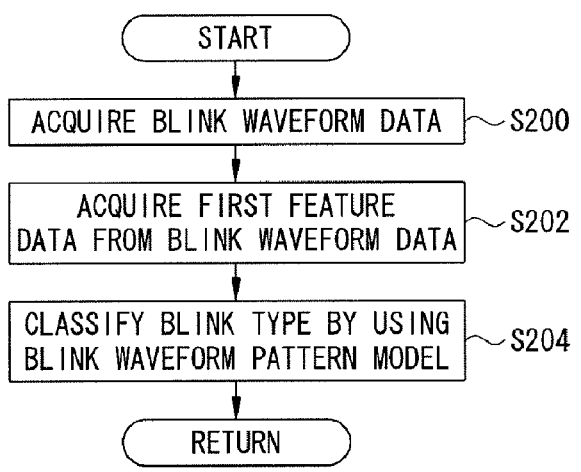
FIG. 14 is a flowchart illustrating a process of extracting first feature data in the warning device 200.

FIG. 14 is a flowchart illustrating a process of extracting the first feature data in the warning device 200.

As shown in FIG. 14, the process of extracting the first feature data moves to step S200 first. The feature data extraction unit 22 acquires the blink electro-oculogram (EOG) waveform data (the blink waveform data) acquired by the blink data acquisition unit 21, and the process moves to step S202.

In step S202, the feature data extraction unit 22 extracts the first feature data obtained from the plurality of feature parameters having different units as the feature data from the blink waveform data acquired in step S200 in a similar manner to the above-described first embodiment. The process then moves to step S204.

In step S204, the blink type identification unit 23 acquires the blink waveform pattern model from the blink waveform pattern model storage unit 21, and identifies the type of blink corresponding to the first feature data extracted in step S202 based on the acquired blink waveform pattern model and the first feature data. The process is then terminated.

In the present embodiment, the HMM is used as the blink waveform pattern model having as an input the first feature data and having as an output a likelihood for the type of blink of a driver.

FIG. 18A is an explanatory view illustrating the second feature data. A unit time (T in the drawing) and a predetermined number of blinks are defined as the analysis interval.

The occurrence ratio of each type of blink is obtained at certain time intervals ($t_s$ in the drawing) while overlapping with the adjacent analysis interval.

A predetermined number (N in the drawing) of the occurrence ratios of each type of blink obtained as described above are merged, so as to generate the second feature data.

A predetermined number of the analysis intervals merged as described above is the sequence of analysis intervals. For example, the second feature data with respect to 8 types of blinks is shown in FIG. 18B.

Although the occurrence ratio of each type of blink is used in the present embodiment, the number of occurrences of each type of blink may be also used.

Next, a process flow for generating the second feature data in the warning device 200 will be described with reference to FIG. 15.

Figure 15:
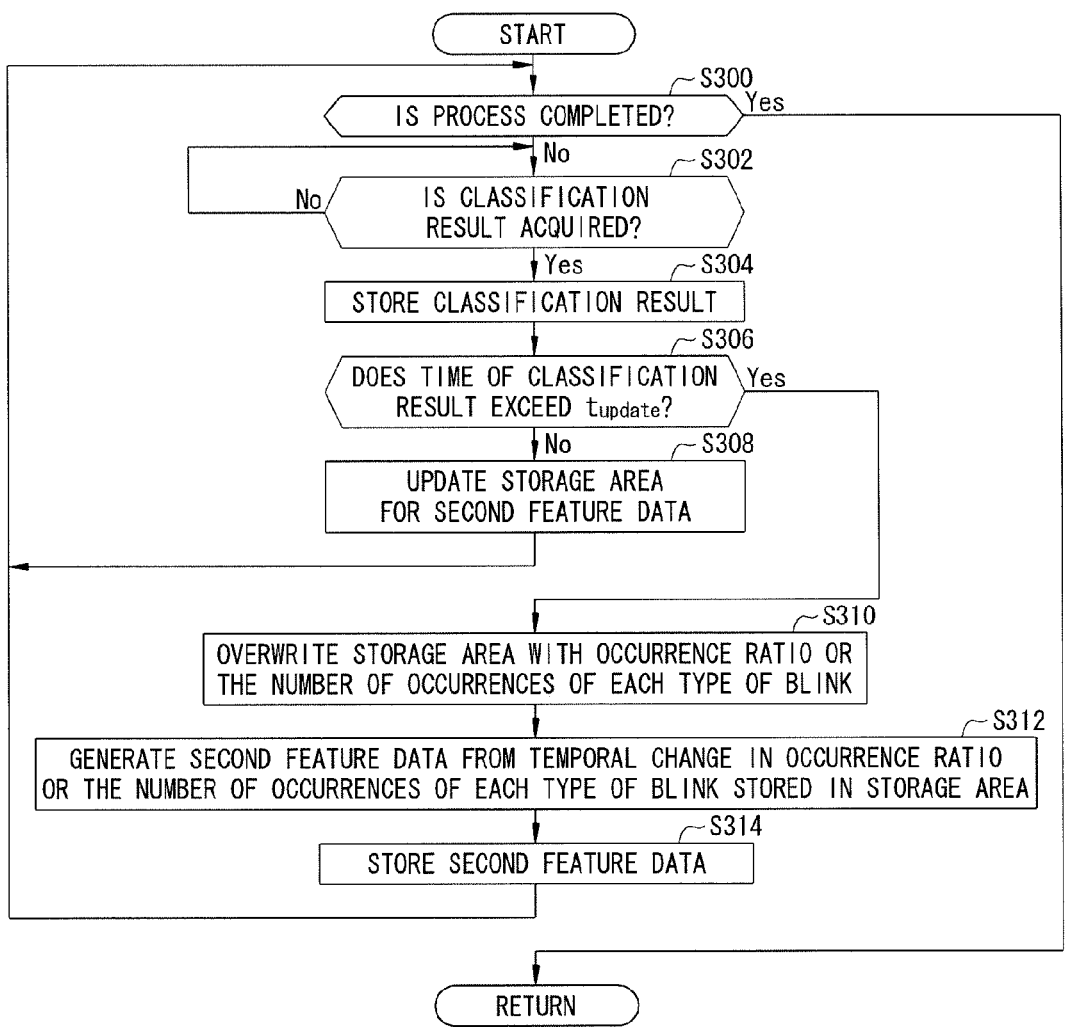
FIG. 15 is a flowchart illustrating a process of generating second feature data in the warning device 200.

FIG. 15 is a flowchart illustrating a process of generating the second feature data in the warning device 200.

As shown in the flowchart of FIG. 15, in the process of generating the second feature data, the feature data generation unit 24 classifies whether or not the process of generating the second feature data has been completed in step S300, first. When it is classified that the process has been completed (Yes), the process is terminated. When it is classified that the process has not been completed (No), the process moves to step S302.

When the process moves to step S302, the feature data generation unit 24 classifies whether or not the identification result has been acquired from the blink type identification unit 23. When it is classified that the identification result has been acquired (Yes), the process moves to step S304. When it is classified that the identification result has not been acquired (No), the process waits until the identification result is acquired.

In the present embodiment, the identification result includes information about the type of blink of the identification result and information about the occurrence time of the blink waveform data corresponding to the first feature data.

When the process moves to step S304, the feature data generation unit 24 stores the identification result in the RAM 52 or a predetermined area of the storage device 60. The process then moves to step S306.

In the present embodiment, the RAM 52 is preferentially used. The storage destination is appropriately changed according to the memory capacity of the RAM 52.

In step S306, the feature data generation unit 24 classifies whether or not the time of the identification result has exceeded the update time of the second feature data ($t_{update}=nt_s$). When it is classified that the time has exceeded the update time (Yes), the process moves to step S310. When it is classified that the time has not exceeded the update time (No), the process moves to step S308. Here, n is an integer number larger than 0, and $t_s$ is an update time interval.

In the present embodiment, the time t and $t_{update}$ are reset (t=0, $t_{update}$=0) when the warning device 200 starts operation.

When the process moves to step S308, the feature data generation unit 24 updates a storage area for the second feature data by using the identification result stored in step S304. The process then moves to step S300.

FIG. 18B illustrates the storage area for the second feature data. The entire second feature data is stored in a storage area 70. In a storage area 71 having a portion of the storage area 70, the number of occurrences of the identification result of the type of blink corresponding to the type of blink indicated by the identification result is added with 1.

When the process moves to step S310, the feature data generation unit 24 obtains the occurrence ratio or the number of occurrences of the identification result of each type of blink based on the number of occurrences of the identification result of each type of blink stored in the storage area, and overwrites the storage area with the occurrence ratio or the number of occurrences. The process then moves to step S312.

In step S312, the feature data generation unit 24 generates the second feature data based on the time variation of the occurrence ratio or the time variation of the number of occurrences of the identification result of each type of blink stored in the storage area, and the process moves to step S314.

In step S314, the feature data generation unit 24 stores the second feature data generated in step S312 in the RAM 52 or a predetermined area of the storage device 60. The process then moves to step S300.

Next, a flow of an arousal state classifying process and a warning process in the warning device 200 will be described with reference to FIG. 16.

Figure 16:
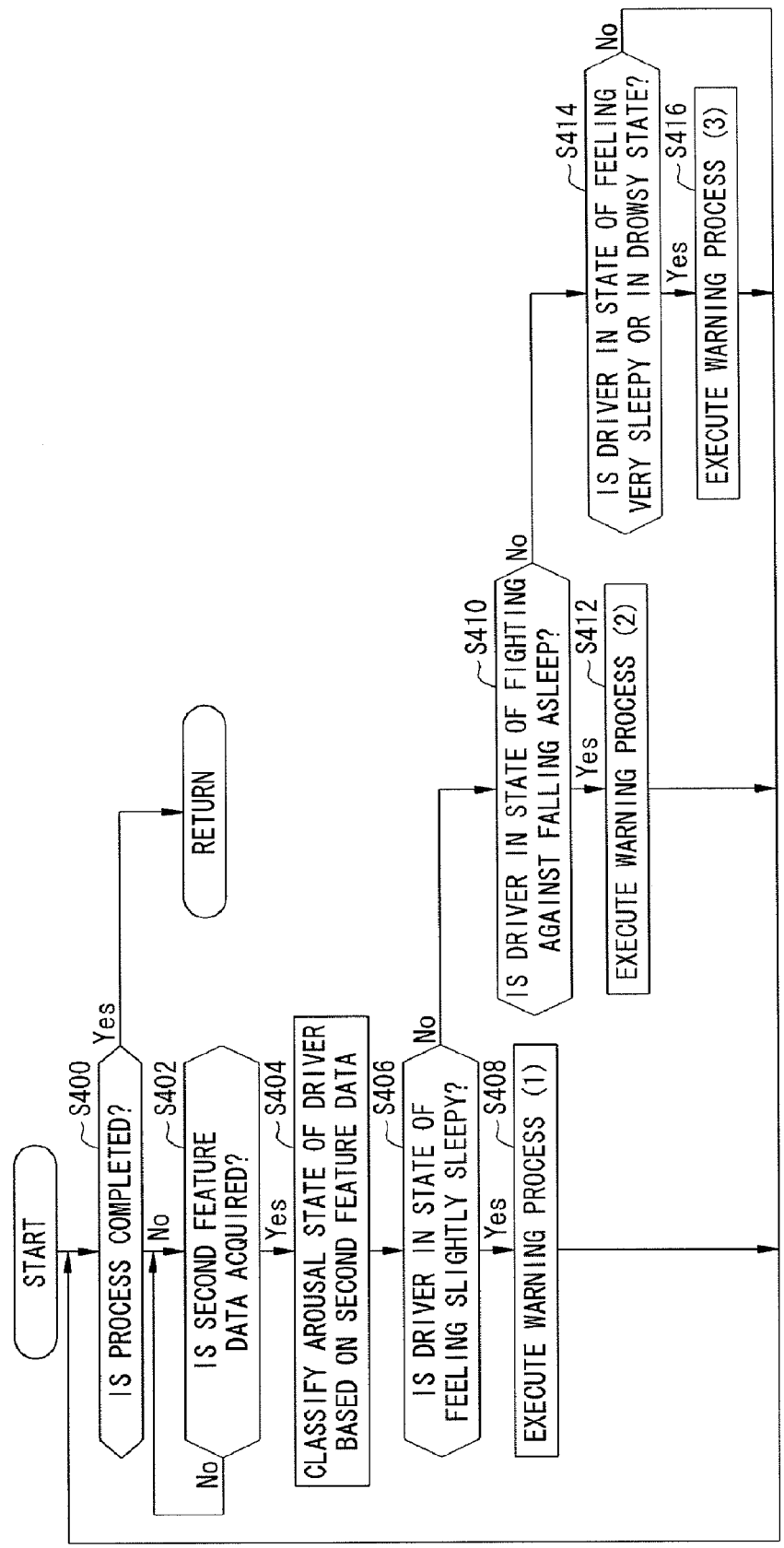
FIG. 16 is a flowchart illustrating a process of classifying an arousal state and a warning process in the warning device 200.

FIG. 16 is a flowchart illustrating the arousal state classifying process and the warning process in the warning device 200.

As shown in the flowchart of FIG. 16, the arousal state classifying process and the warning process moves to step S400 first. The arousal state classification unit 26 classifies whether or not the arousal state classifying process has been completed. When it is classified that the process has been completed (Yes), the process is terminated. When it is classified that the process has not been completed (No), the process moves to step S402.

When the process moves to step S402, the arousal state classification unit 26 classifies whether or not the second feature data has been acquired from the feature data generation unit 24. When it is classified that the second feature data has been acquired (Yes), the process moves to step S404. When it is classified that the second feature data has not been acquired (No), the process waits until the second feature data is acquired.

When the process moves to step S404, the arousal state classification unit 26 classifies the arousal state of a driver based on the second feature data acquired in step S402 and the arousal state pattern model stored in the arousal state pattern model storage unit 25. The process then moves to step S406.

In the present embodiment, the HMM is used as the arousal state pattern model having as an input the second feature data and having as an output a likelihood for the arousal state information indicating the arousal state of the driver.

In step S406, the warning unit 27 classifies whether or not the driver feels sleepy based on the classification result in step S404. When it is classified that the driver feels sleepy (Yes), the process moves to step S408. When it is classified that the driver does not feel sleepy (No), the process moves to step S410.

When the process moves to step S408, the warning unit 27 executes a warning process (1), and the process moves to step S400. When the warning process (1) is executed, a voice message to recommend the driver to take a rest is output.

Meanwhile, when the process moves to step S410, the warning unit 27 classifies whether or not the driver is in the state of fighting against falling asleep. When it is classified that the driver is in the state of fighting against falling asleep (Yes), the process moves to step S412. When it is classified that the driver is not in the state of fighting against falling asleep (No), the process moves to step S414.

When the process moves to step S412, the warning unit 27 executes a warning process (2), and the process moves to step S400. When the warning process (2) is executed, a warning sound and a warning message with a relatively loud sound volume (for example, a sound volume of 50%) are output from a speaker placed in a vehicle.

Meanwhile, when the process moves to step S414, the warning unit 27 classifies whether or not the driver is in the low arousal state in which the driver feels very sleepy or in the drowsy state. When it is classified that the driver is in the low arousal state in which the driver feels very sleepy or in the drowsy state (Yes), the process moves to step S416. When it is classified that the driver is not in the low arousal state or in the drowsy state (No), the process moves to step S400.

When the process moves to step S416, the warning unit 27 executes a warning process (3), and the process moves to step S400. When the warning process (3) is executed, a warning sound and a warning message with a very loud sound volume (for example, a sound volume of 70% or more) are output from a speaker placed in a vehicle.

Although the electro-oculogram (EOG) waveform data is used as the blink waveform data, the case of using the moving picture of eye region instead of the electro-oculogram (EOG) waveform data will be described.

The blink data acquisition unit 20 shoots the face image of a driver who is sitting in the driver's seat frame by frame in real time by a CCD camera installed on the inner mirror in an automobile.

The shot face images are output as digital face video data. The CCD camera may be installed at a position other than the inner mirror, such as the positions of the steering column, the center panel, and the front pillar so long as the image including the entire face of an object person to be shot can be captured.

The feature data extraction unit 22 extracts the video data of the eye portion from the face video data of the driver shot by the blink data acquisition unit 20 by using an SVM, and then extracts the feature data from the extracted video data of the eye portion.

Although the SVM is used to extract the video data of the eye region from the video data of the driver's face in the aforementioned example, the eye region may also be extracted by using an algorithm for detecting another organ of the face.

Specifically, the feature data is extracted by trimming an extraction region image of 11 pixels in width and 30 pixels in height from each blink image data having the video data of the right eye portion with the eyeball as the center, calculating the sum of brightness values of each pixel line (11 pixels in width) of the extraction region image, and employing the data on the calculated sum of brightness values (for the video of one blink) as the feature data in a similar manner to the above-described first embodiment.

The feature data further includes a frequency spectrum component obtained by converting the frequency of an eye region image, an inter-frame difference component between the current frame for the frequency spectrum component and its previous and subsequent frames, a Mel cepstrum (MFCC) component for an eye region image, an intra-frame moment component and an inter-frame moment component for an eye region image, and a combination thereof.

In the warning device 200, the feature data extraction unit 22 acquires the blink waveform data from the blink data acquisition unit 20 (step S200).

The first feature data obtained from three feature parameters of a peak height (distance) x1 of a blink waveform, a rise time x2 from blink start to the peak height, and a fall time x3 from the peak height to blink end is extracted as the feature data from the acquired blink waveform data in a similar manner to the first feature data extraction unit 11 of the pattern model generating device 100 in the above-described first embodiment (step S202).

When the feature data is extracted, the blink type identification unit 23 acquires the blink waveform pattern model stored in the storage device 60 via the blink waveform pattern model storage unit 21, and identifies the type of blink based on a likelihood for each type of blink (Class 1 to Class 12) output from the blink waveform pattern model in relation to the input of the first feature data to the acquired blink waveform pattern model (step S204). The identification result is output to the feature data generation unit 24.

Every time the identification result is acquired (the "Yes" branch from step S302), the feature data generation unit 24 stores the identification result in the RAM 52 or a predetermined area of the storage device 60 (step S304).

As described above, the identification result is the information including acquisition time information of the blink waveform data corresponding to the first feature data at the time of identification, and information about the identified type of blink.

It is then classified whether or not the time of the identification result has exceeded the update time of the second feature data ($t_{update} = nt_s$) (step S306).

When it is classified that the time of the identification result has exceeded the update time of the second feature data (the "Yes" branch from step S306), the occurrence ratio or the number of occurrences of the identification result of each type of blink is obtained based on the number of occurrences of the identification result of each type of blink stored in the storage area, and the storage area is overwritten with the occurrence ratio or the number of occurrences (step S310).

The second feature data is generated based on the time variation of the occurrence ratio or the time variation of the number of occurrences of the identification result of each type of blink stored in the storage area as described above (step S312).

The second feature data is stored in the RAM 52 or a predetermined area of the storage device 60 (step S314).

On the other hand, when it is classified that the time of the identification result has not exceeded the update time of the second feature data (the "No" branch from step S306), the feature data generation unit 24 updates the storage area for the second feature data by using the identification result stored in step S304 (step S308).

When the second feature data is acquired from the feature data generation unit 24 (the "Yes" branch from step S402), the arousal state classification unit 26 classifies the arousal state of the driver based on the second feature data and the arousal state pattern model stored by the arousal state pattern model storage unit 25 (step S404).

In the example shown in the drawing, the driver is classified to feel slightly sleepy for a certain time from the start (the "Yes" branch from step S406). The warning unit 28 executes a warning process (1), and outputs a voice message to recommend the driver to take a rest (step S408).

The driver is classified to feel sleepy after the certain time from the start to the middle phase (the "Yes" branch from step S410). The warning unit 28 executes a warning process (2), and outputs a warning sound with a sound volume of 50% of the maximum sound volume (step S412).

The driver is classified to feel very sleepy or be in the drowsy state from the middle phase to the latter half (the "Yes" branch from step S414). The warning unit 28 executes a warning process (3), and outputs a warning sound with a sound volume of 70% or more of the maximum sound volume (step S416).

Although the electro-oculogram (EOG) waveform data is used as the blink waveform data in the above description, the case of using the moving picture of eye region instead of the electro-oculogram (EOG) waveform data will be described next.

The feature data extraction unit 22 acquires the moving picture of eye region from the blink data acquisition unit 21 (step S200). The feature data extraction unit 22 uses the SVM to detect the blink video data of the right eye from the acquired moving picture of the eyes, and extracts the feature data from the detected blink video data (step S202).

The feature data is extracted by using the same method as that of the first feature data extraction unit 11 of the arousal state classification model generating device 100 in the above-described first embodiment.

That is, the data on the sum of brightness values of each of all the 30 lines of the extraction region image in each blink image data having the blink video data corresponding to one blink is extracted as the feature data.

The feature data further includes a frequency spectrum component obtained by converting the frequency of an eye region image, an inter-frame difference component between the current frame for the frequency spectrum component and its previous and subsequent frames, a Mel cepstrum (MFCC) component for an eye region image, an intra-frame moment component and an inter-frame moment component for an eye region image, and a combination thereof.

Next, to confirm the effect of the present invention, an example of a result of classifying the arousal state of an object person will be shown in FIG. 19 to FIG. 21.

Figure 19A:
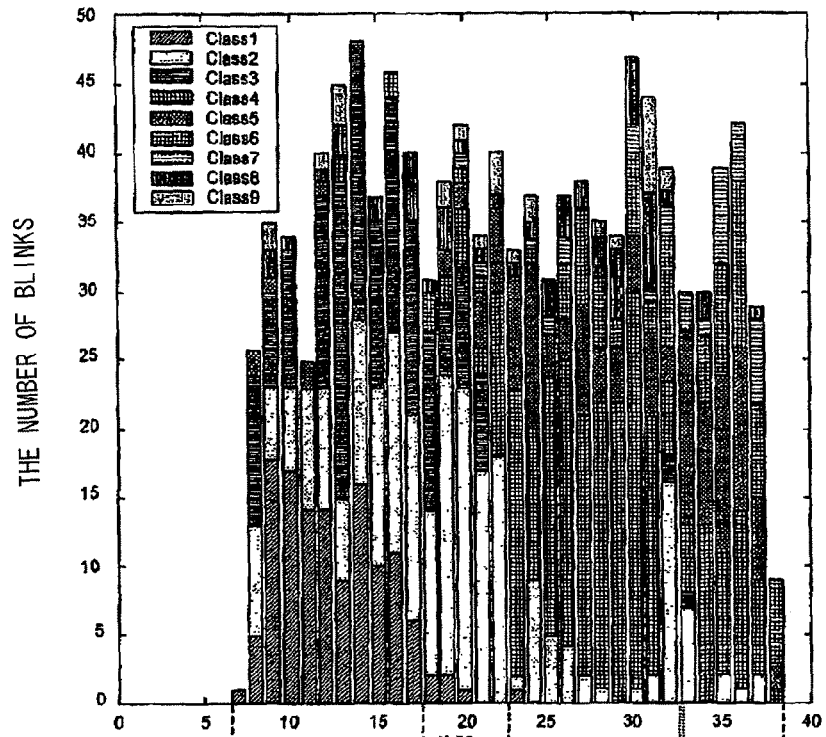
FIG. 19 is a view illustrating an example of the occurrence frequency of each type of blink in a certain time interval and a result of classifying the arousal state of a specific object person A when the blink waveform pattern model of the object person A is used, in a case of using electro-oculogram (EOG) waveform data as blink waveform data.

FIG. 19A is a view illustrating an example of the occurrence frequency of each type of blink within a certain time interval obtained based on the identification result of the type of blink waveform of a specific object person (referred to as object person A below) identified by the blink type identification unit 23 when the blink waveform pattern model and the arousal state pattern model of the object person A are used, in a case of using the electro-oculogram (EOG) waveform data as the blink waveform data.

Figure 19B:
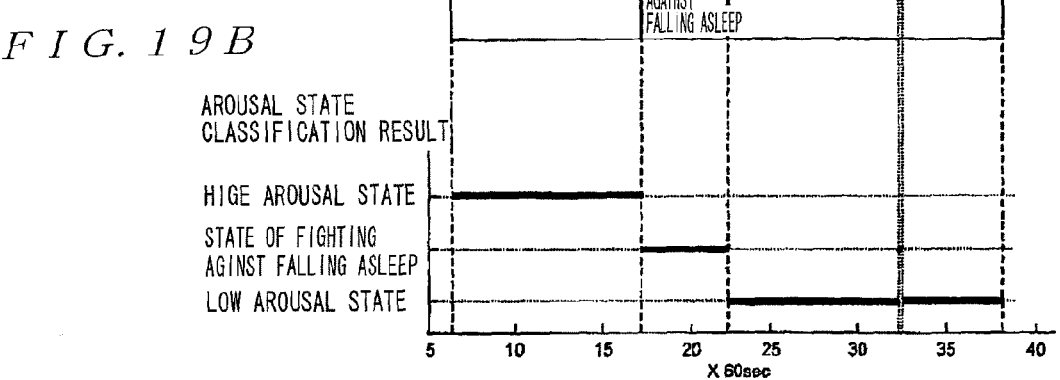

FIG. 19B illustrates a result of classifying the arousal state of the object person A by the arousal state classification unit 26 based on the second feature data generated by the feature data generation unit 24 from the identification result of the type of blink waveform described above and the arousal state pattern model stored in the arousal state pattern model storage unit 25.

Figure 20A:
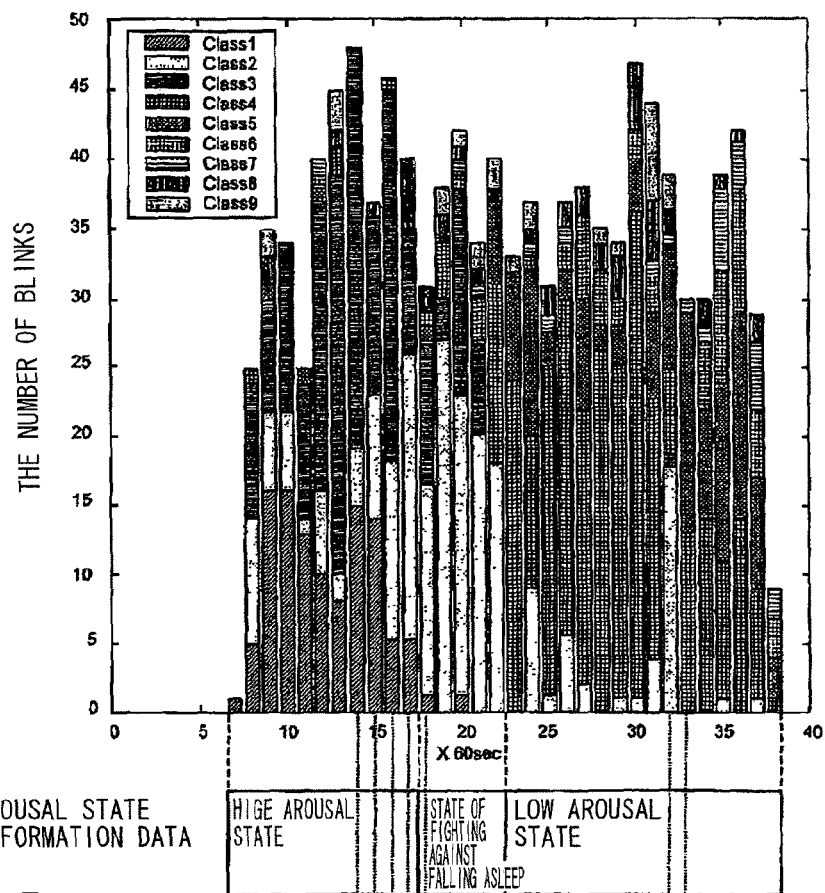
FIG. 20 is a view illustrating an example of the occurrence frequency of each type of blink in a certain time interval and a result of classifying the arousal state of a specific object person A when the blink waveform pattern model of the object person A is used, in a case of using moving picture of eye region as blink waveform data.

FIG. 20A is a view illustrating an example of the occurrence frequency of each type of blink within a certain time interval obtained based on the identification result of the type of blink waveform of the same specific object person A as that in FIG. 19 identified by the blink type identification unit 23 when the blink waveform pattern model and the arousal state pattern model of the object person A are used, in a case of using the moving picture of eye region as the blink waveform data.

Figure 20B:
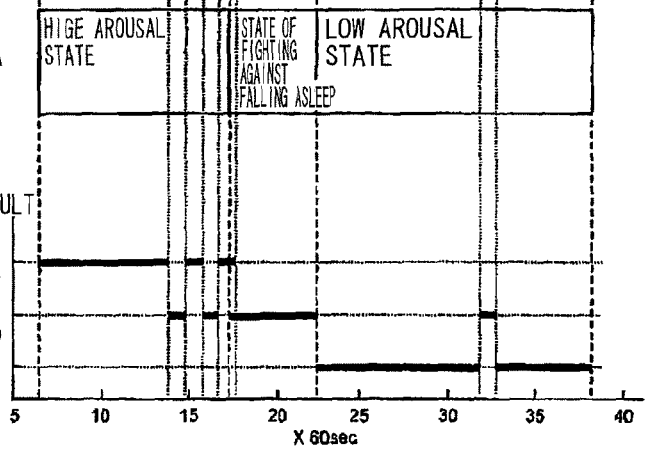

FIG. 20B illustrates a result of classifying the arousal state of the object person A by the arousal state classification unit 26 based on the second feature data generated by the feature data generation unit 24 from the identification result of the type of blink waveform described above and the arousal state pattern model stored in the arousal state pattern model storage unit 25.

From the results, in both the cases of using the electro-oculogram (EOG) waveform data and the moving picture of eye region as the blink waveform data, the arousal state classification results shown in FIG. 19B and FIG. 20B reproduce the arousal state of the object person A speculated from the determination, consideration, and observation record using the physiological and biological data in the experiment in FIG. 9.

Furthermore, in the arousal state classification results, the more detailed arousal state transition of the object person A than the arousal state speculated from the determination, consideration, and observation record using the physiological and biological data in the experiment shown in FIG. 9 is classified, so that the sign of a change in the arousal state can be captured in an early phase.

On the other hand, FIG. 21A is a view illustrating an example of the occurrence frequency of each type of blink within a certain time interval obtained based on the identification result of the type of blink waveform of the object person A identified by the blink type identification unit 23 when the blink waveform pattern models and the arousal state pattern models of unspecified object persons are used, in a case of using the moving picture of eye region as the blink waveform data.

The learning data used for generating the blink waveform pattern models of unspecified object persons by the arousal state classification model generating device 100 includes the first feature data extracted from the blink waveform data (the moving picture of eye region) of four object persons (object persons A, B, C and D), and the blink waveform identification information data of the four object persons.

FIG. 21D illustrates a result of classifying the arousal state of the object person A by the arousal state classification unit 26 based on the second feature data generated by the feature data generation unit 24 from the identification result of the type of blink waveform described above and the arousal state pattern models of unspecified object persons stored in the arousal state pattern model storage unit 25.

The arousal state pattern models of unspecified object persons are generated by the arousal state classification model generating device 100 by using the learning data of the four object persons (the object persons A, B, C and D).

Even when the blink waveform pattern models and the arousal state pattern models of the unspecified object persons are used, the arousal state classification result shown in FIG. 21D reproduces FIG. 21B showing the arousal state of the object person A speculated from the determination, consideration, and observation record using the physiological and biological data in the experiment.

Accordingly, by using the models of unspecified object persons for the blink waveform pattern model and the arousal state pattern model, the arousal state transition can be classified without preparing a dedicated model for each object person in advance.

In the aforementioned example, the models of a specific object person or the models of unspecified object persons are used for both the blink waveform pattern model and the arousal state pattern model. However, the models of a specific object person may be used for one of the blink waveform pattern model and the arousal state pattern model, and the models of unspecified object persons may be used for the other of the models.

Furthermore, FIG. 21C, FIG. 21D, and FIG. 22 illustrate examples of comparing the classification results of the arousal state of the object person according to the present invention and according to the related art in Patent Document 1. In the related art as the target of comparison, a predetermined threshold index is set for the occurrence frequencies of a plurality of specific types of blink waveform patterns, to determine the arousal state of the object person.

FIG. 21C illustrates an example of classifying the arousal state of the object person A by using the related art. The moving picture of eye region is employed as the blink waveform data of the object person A. The blink waveform pattern models of the above unspecified object persons are used as the blink waveform pattern model.

The arousal state is classified by setting a predetermined threshold index for the occurrence frequency of each type of blink within a certain time interval.

To be more specific, the threshold index is set to best match FIG. 21B showing the arousal state of the object person A speculated from the classification, consideration, and observation record using the physiological and biological data in the experiment.

As a result, FIG. 21D shows a similar result to that of FIG. 21C showing the classification result of the arousal state of the object person A according to the present invention although there is a certain difference when compared with FIG. 21C.

FIG. 22A is a view illustrating an example of the occurrence frequency of each type of blink within a certain time interval obtained based on the identification result of the type of blink waveform of the object person B identified by the blink type identification unit 23 when the blink waveform pattern models and the arousal state pattern models of the unspecified object persons are used, in a case of using the moving picture of eye region as the blink waveform data.

FIG. 22B illustrates the arousal state of the object person B speculated from the classification, consideration, and observation record using the physiological and biological data in the experiment.

FIG. 22C illustrates an example of classifying the arousal state of the object person B by using the threshold index used for the object person A according to the related art.

FIG. 22D illustrates an example of classifying the arousal state of the object person B according to the present invention.

In the related art, the arousal state is occasionally falsely classified to be the low arousal state and the high arousal state respectively in a high arousal state interval and a low arousal state interval in the arousal state information data. Also, the arousal state cannot be classified to be the state of fighting against falling asleep in an interval of state of fighting against falling asleep.

That is, it is shown that the threshold index used for a specific object person cannot be used for another object person.

On the other hand, in the present invention, the arousal state is falsely classified to be the state of fighting against falling asleep for a very short period of time in the high arousal state interval in the arousal state information data, and the arousal state is falsely classified to be the high arousal state for a very short period of time in the low arousal state interval in the arousal state information data.

The arousal state is classified to be the state of fighting against falling asleep in the latter half of interval of fighting against falling asleep. As described above, the classification result of the arousal state according to the present invention is closer to the arousal state information data than that of the related art. That is, it is shown that the classification using the models of unspecified object persons is possible.

Although speech recognition is known as the application of identification using a statistical pattern model as represented by the HMM, the target feature values in the arousal state classification in the present invention and in the speech recognition are essentially different from each other.

To be more specific, the recognition target in the speech recognition is generally a phoneme uttered by a human. A difference between phonemes as the feature has a wide distribution due to a difference in an utterer and an uttering situation even when the phonemes are the same phonemes. However, the feature of each phoneme is discrete.

To the contrary, since the blink data is physiological and biological data, the blink waveform as the recognition target successively changes from a certain type to another type according to a change in the arousal state of an object person. A difference between the blink types is essentially successive.

The feature values as the recognition targets thereof have an essential difference as described above. The arousal state classification in the present invention is essentially different from the pattern recognition in the speech recognition in that the blink waveform which successively changes from a certain type to another type according to the arousal state of the object person is targeted, and the occurrence frequency of each type of blink waveform within a certain time interval is identified by using the pattern models.

In the aforementioned second embodiment, the blink data acquisition unit 20 corresponds to blink data acquisition means. The blink waveform pattern model stored in the blink waveform pattern model storage unit 21 corresponds to a first pattern model. The feature data extraction unit 22 corresponds to first feature data extraction means. The blink type identification unit 23 corresponds to blink waveform identification means. The feature data generation unit 24 corresponds to second feature data generation means. The arousal state pattern model stored in the arousal state pattern model storage unit 25 corresponds to a second pattern model. The arousal state classification unit 26 corresponds to arousal state classification means. The warning unit 27 corresponds to warning means.

In the aforementioned second embodiment, step S200 corresponds to a step of acquiring blink data. Step S202 corresponds to a step of extracting first feature data. Step S204 corresponds to a step of identifying a blink waveform. Steps S300 to S314 correspond to a step of generating second feature data. Steps S400 to S404 correspond to a step of classifying an arousal state.

Although the example in which the pattern model is composed of the HMM is described in the above-described first embodiment, the present invention is not limited thereto. The pattern model may be also composed of another statistical model such as an SVM and a neutral network.

In the above-described first and second embodiments, the sum of brightness of each line of the extraction region image trimmed from the moving picture of eye region is extracted as the first feature data. However, the present invention is not limited thereto. Another feature value, for example, a frequency spectrum component obtained by performing a Fourier transform on blink image data may be extracted as the feature value.

Although the arousal state of an object person (a driver) is classified based on the second feature data in the above-described second embodiment, the present invention is not limited thereto. Another state of the object person, such as a tension state and a fatigue state, may be also classified based on the second feature data.

In the above-described first and second embodiments, the second feature data is composed of only the time variation of the occurrence ratio or the number of occurrences of each specific type of blink waveform in the sequence of analysis intervals. However, a feature relating to the arousal state, such as a time variation of the number of blinks or a time variation of the accumulated value of eye-closing time in the sequence of analysis intervals, may be added thereto.

INDUSTRIAL APPLICABILITY

In the present invention, the arousal state can be classified with high accuracy based on the data on the occurrence ratio of each of the specific types of blinks in the sequence of analysis intervals in addition to the change in the occurrence frequencies of the specific types of blinks within a predetermined time such as the occurrence frequencies of specific types of blinks and the blink bursts of a specific type of blink, which is considered as effective in classifying the arousal state.

Accordingly, the arousal level (state) of a driver transiting to the drowsy state before completely falling asleep, or the arousal level (state) of fighting against falling asleep can be detected.

The present invention is thereby preferably used in the technical field of preventing an accident from occurring by warning an object person who is likely to fall asleep with a warning sound or flashing lights.

Furthermore, it is possible to assist the driving of a driver by classifying the tension state or fatigue state of the driver based on the data on the occurrence frequency information of the specific types of blinks in a similar manner.

The invention claimed is:

1. An arousal state classification model generating device for generating a statistical model to determine an arousal state of an object person, the arousal state classification model generating device characterized by comprising:
    learning data storage means for storing first feature data extracted from blink data of at least one eye of each object person at the time of blinking, and blink waveform identification information data in which blink waveform identification information indicating a specific type of blink waveform is provided to each blink in the blink data;
    blink waveform pattern model generation means for learning a statistical model by using as learning data the first feature data and the blink waveform identification information data stored in the learning data storage means, and generating a first pattern model having as an input the first feature data and having as an output a likelihood for the blink waveform identification information in relation to the first feature data;
    feature data generation means for generating second feature data including data on an occurrence ratio of each of the specific types of blink waveforms in an analysis interval based on the blink waveform identification information data stored in the learning data storage means; and
    arousal state pattern model generation means for learning a statistical model by using as learning data the second feature data generated by the feature data generation means and arousal state information data in which arousal state information indicating the arousal state of the object person is provided to each sequence of the analysis intervals, and generating a second pattern model having as an input the second feature data and having as an output a likelihood for the arousal state information in relation to the second feature data.

2. The arousal state classification model generating device according to claim 1, characterized in that the blink data is electro-oculogram (EOG) waveform data or moving picture of eye region.

3. The arousal state classification model generating device according to any one of claims 1 and 2, characterized in that the data on the occurrence ratio is a time variation of the occurrence ratio or a time variation of the number of occurrences.

4. The arousal state classification model generating device according to claim 1, characterized in that an HMM (Hidden Markov Model) is used for the statistical model.

5. The arousal state classification model generating device according to claim 1, further comprising:
    blink data storage means for storing the blink data of at least one eye of the object person at the time of blinking;
    feature data extraction means for extracting the first feature data from the blink data acquired from the blink data storage means;
    first pattern model storage means for storing the first pattern model generated by the blink waveform pattern model generation means;
    second feature data storage means for storing the second feature data generated by the feature data generation means; and
    second pattern model storage means for storing the second pattern model generated by the arousal state pattern model generation means.

6. An arousal state classifying device for classifying an arousal state of an object person, the arousal state classifying device characterized by comprising:
    blink data acquisition means for acquiring blink data of at least one eye of the object person at the time of blinking;
    a first pattern model generated by the arousal state classification model generating device according to claim 1;
    first feature data extraction means for extracting first feature data corresponding to the first pattern model from the blink data acquired by the blink data acquisition means;
    blink waveform identification means for identifying a specific type of blink waveform corresponding to the first feature data extracted by the first feature data extraction means based on the first feature data and the first pattern model;
    second feature data generation means for generating second feature data including data on an occurrence ratio of each of the specific types of blink waveforms based on an identification result by the blink waveform identification means with respect to the blink data of the object person acquired in a sequence of analysis intervals;

a second pattern model generated by the arousal state classification model generating device; and arousal state classification means for classifying the arousal state of the object person based on the second feature data generated by the second feature data generation means and the second pattern model.

7. The arousal state classifying device according to claim 6, characterized in that the blink data is electro-oculogram (EOG) waveform data or moving picture of eye region.

8. The arousal state classifying device according to any one of claims 4 and 5, characterized in that the data on the occurrence ratio is a time variation of the occurrence ratio or a time variation of the number of occurrences.

9. The arousal state classifying device according to any one of claims 4 to 6, characterized in that an HMM (hidden Markov model) is used for the first pattern model and the second pattern model.

10. A warning device comprising:
the arousal state classifying device according to claim 6; and
warning means for warning the object person based on a classification result of the arousal state in the arousal state classifying device.

11. A vehicle comprising the warning device according to claim 10.

12. An arousal state classification model generating method for generating a statistical model to determine an arousal state of an object person, the arousal state classification model generating method characterized by comprising:
a learning data storage step of storing first feature data extracted from blink data of at least one eye of each object person at the time of blinking, and blink waveform identification information data in which blink waveform identification information indicating a specific type of blink waveform is provided to each blink in the blink data;
a blink waveform pattern model generation step of learning a statistical model by using as learning data the first feature data and the blink waveform identification information data stored in the learning data storage step, and generating a first pattern model having as an input the first feature data and having as an output a likelihood for the blink waveform identification information in relation to the first feature data;
a feature data generation step of generating second feature data including data on an occurrence ratio of each of the specific types of blink waveforms in an analysis interval based on the blink waveform identification information data stored in the learning data storage step; and
an arousal state pattern model generation step of learning a statistical model by using as learning data the second feature data generated in the feature data generation step and arousal state information data in which arousal state information indicating the arousal state of the object person is provided to each sequence of the analysis intervals, and generating a second pattern model having as an input the second feature data and having as an output a likelihood for the arousal state information in relation to the second feature data.

13. The arousal state classification model generating method according to claim 12, characterized in that the data on the occurrence ratio is a time variation of the occurrence ratio or a time variation of the number of occurrences.

14. The arousal state classification model generating method according to any one of claims 12 and 13, further comprising:
a blink data storage step of storing the blink data of at least one eye of the object person at the time of blinking in blink data storage means;
a feature data extraction step of extracting the first feature data from the blink data stored in the blink data storage means;
a first pattern model storage step of storing the first pattern model generated in the blink waveform pattern model generation step;
a second feature data storage step of storing the second feature data generated in the feature data generation step; and
a second pattern model storage step of storing the second pattern model generated in the arousal state pattern model generation step.

15. An arousal state classifying method for classifying an arousal state of an object person, the arousal state classifying method comprising:
a blink data acquisition step of acquiring blink data of at least one eye of the object person at the time of blinking;
a first feature data extraction step of extracting first feature data corresponding to a first pattern model generated in the arousal state classification model generating method according to claim 12 from the blink data acquired in the blink data acquisition step;
a blink waveform identification step of identifying a specific type of blink waveform corresponding to the first feature data extracted in the first feature data extraction step based on the first feature data and the first pattern model;
a second feature data generation step of generating second feature data including data on an occurrence ratio of each of the specific types of blink waveforms based on an identification result in the blink waveform identification step with respect to the blink data of the object person acquired in a sequence of analysis intervals; and
an arousal state classification step of classifying the arousal state of the object person based on the second feature data generated in the second feature data generation step and a second pattern model generated in the arousal state classification model generating method.

16. The arousal state classifying method according to claim 15, characterized in that the data on the occurrence ratio is a time variation of the occurrence ratio or a time variation of the number of occurrences.

17. A non-transitory computer readable storage medium that stores an arousal state classification model generating program for generating a statistical model to determine an arousal state of an object person, the program when executed causing a computer to perform:
a learning data storage step storing first feature data extracted from blink data of at least one eye of each object person at the time of blinking, and blink waveform identification information data in which blink waveform identification information indicating a specific type of blink waveform is provided to each blink in the blink data;
a blink waveform pattern model generation step learning a statistical model by using as learning data the first feature data and the blink waveform identification information data stored in the learning data storage step, and generating a first pattern model having as an input the first feature data and having as an output a likelihood for the blink waveform identification information in relation to the first feature data;

a feature data generation step generating second feature data including data on an occurrence ratio of each of the specific types of blink waveforms an analysis intervals based on the blink waveform identification information data stored by the learning data storage step; and an arousal state pattern model generation step learning a statistical model by using as learning data the second feature data generated by the feature data generation step and arousal state information data in which arousal state information indicating the arousal state of the object person is provided to each of the sequences of analysis intervals, and generating a second pattern model having as an input the second feature data and having as an output a likelihood for the arousal state information in relation to the second feature data.

18. The non-transitory computer readable storage medium according to claim 17, wherein the data on the occurrence ratio is a time variation of the occurrence ratio or a time variation of the number of occurrences.

19. The non-transitory computer readable storage medium according claim 17 or claim 18, the program when executed causing the computer to perform:

a blink data storage step storing the blink data of at least one eye of the object person at the time of blinking;

a feature data extraction step extracting the first feature data from the blink data stored in the blink data storage step;

a first pattern model storage step storing the first pattern model generated by the blink waveform pattern model generation step;

a second feature data storage step storing the second feature data generated by the feature data generation step; and a second pattern model storage step storing the second pattern model generated by the arousal state pattern model generation step.

20. A non-transitory computer readable storage medium that stores an arousal state classifying program for classifying an arousal state of an object person, the program when executed causing a computer to perform:

a blink data acquisition step acquiring blink data of at least one eye of the object person at the time of blinking;

a first feature data extraction step extracting first feature data corresponding to a first pattern model generated by the arousal state classification model generating program according to claim 17 from the blink data acquired by the blink data acquisition step;

a blink waveform identification step identifying a specific type of blink waveform corresponding to the first feature data extracted in the first feature data extraction step based on the first feature data and the first pattern model;

a second feature data generation step generating second feature data including data on an occurrence ratio of each of the specific types of blink waveforms based on an identification result by the blink waveform identification step with respect to the blink data of the object person acquired in a sequence of analysis intervals; and an arousal state classification step classifying the arousal state of the object person based on the second feature data generated in the second feature data generation step and a second pattern model generated by the arousal state classification model generating program.

21. The non-transitory computer readable storage medium according to claim 20, wherein the data on the occurrence ratio is a time variation of the occurrence ratio or a time variation of the number of occurrences.

* * * * *

UNITED STATES PATENT AND TRADEMARK OFFICE
CERTIFICATE OF CORRECTION

PATENT NO. : 8,400,313 B2
APPLICATION NO. : 12/522505
DATED : March 19, 2013
INVENTOR(S) : Yoshihiro Noguchi et al.

Page 1 of 1

It is certified that error appears in the above-identified patent and that said Letters Patent is hereby corrected as shown below:

ON THE TITLE PAGE:

Item (30), correct the Foreign Application Priority Data to read as follows:

--Jan. 19, 2007      (JP) .................... 2007-009729--.

Signed and Sealed this
Twenty-seventh Day of August, 2013

Teresa Stanek Rea
*Acting Director of the United States Patent and Trademark Office*